United States Patent [19]
Kirlin et al.

[11] Patent Number: 6,126,996
[45] Date of Patent: *Oct. 3, 2000

[54] METAL COMPLEX SOURCE REAGENTS FOR CHEMICAL VAPOR DEPOSITION

[75] Inventors: Peter S. Kirlin, Bethel; Duncan W. Brown, Wilton; Thomas W. Baum, New Fairfield, all of Conn.; Brian A. Vaarstra, Nampa, Id.; Robin A. Gardiner, Bethel, Conn.

[73] Assignee: Advanced Technology Materials, Inc., Danbury, Conn.

[*] Notice: This patent is subject to a terminal disclaimer.

[21] Appl. No.: 08/990,943

[22] Filed: Dec. 15, 1997

Related U.S. Application Data

[60] Division of application No. 08/477,797, Jun. 7, 1995, Pat. No. 5,840,897, and a continuation-in-part of application No. 08/414,504, Mar. 31, 1995, Pat. No. 5,820,664, which is a continuation-in-part of application No. 08/280,143, Jul. 25, 1994, Pat. No. 5,536,323, which is a continuation of application No. 07/927,134, Aug. 7, 1992, abandoned, which is a continuation-in-part of application No. 07/807,807, Dec. 13, 1991, Pat. No. 5,204,314, which is a continuation of application No. 07/549,389, Jul. 6, 1990, abandoned, said application No. 08/477,797, is a continuation-in-part of application No. 08/181,800, Jan. 18, 1994, Pat. No. 5,453,494, which is a continuation-in-part of application No. 07/918,141, Jul. 22, 1992, Pat. No. 5,280,012, which is a continuation of application No. 07/615,303, Nov. 19, 1990, abandoned, which is a division of application No. 07/581,631, Sep. 12, 1990, Pat. No. 5,225,561, which is a continuation-in-part of application No. 07/549,389, Jul. 6, 1990, abandoned.

[51] Int. Cl.$^7$ .................................................. C23C 16/00
[52] U.S. Cl. ......................... 427/252; 556/40; 556/136; 556/57; 534/15; 427/255.21; 427/255.32; 549/3; 549/257
[58] Field of Search .................... 424/1.11, 1.65; 534/7, 10–16; 505/100, 120, 121, 124, 125, 734; 546/256, 257, 259; 252/182.23; 106/287.17, 287.19; 556/44, 55, 114, 175, 40, 42, 57, 136; 562/607; 118/726; 261/154, 100, 106; 549/3, 206; 564/502, 199, 169; 568/303; 427/99, 252, 255.21, 255.32

[56] References Cited

U.S. PATENT DOCUMENTS

| | | |
|---|---|---|
| 3,549,412 | 12/1970 | Frey, Jr. et al. . |
| 3,894,164 | 7/1975 | Dismukes et al. . |
| 3,978,272 | 8/1976 | Donley . |
| 4,148,940 | 4/1979 | Breininger et al. . |
| 4,180,386 | 12/1979 | McCormack et al. . |
| 4,501,602 | 2/1985 | Miller et al. . |
| 4,732,110 | 3/1988 | Parsons . |
| 4,735,852 | 4/1988 | Osada . |
| 4,804,649 | 2/1989 | Sherif . |
| 4,837,609 | 6/1989 | Gurvitch et al. . |
| 4,845,308 | 7/1989 | Womack, Jr. . |
| 4,869,598 | 9/1989 | McDonald . |
| 4,870,052 | 9/1989 | Engler et al. . |
| 4,880,770 | 11/1989 | Mir et al. . |
| 4,882,312 | 11/1989 | Mogro-Campero . |
| 4,908,346 | 3/1990 | Strom et al. . |
| 4,908,348 | 3/1990 | Hung et al. . |
| 4,915,988 | 4/1990 | Erbil . |
| 4,916,115 | 4/1990 | Mantese et al. . |
| 4,918,051 | 4/1990 | Mantese et al. . |

(List continued on next page.)

FOREIGN PATENT DOCUMENTS

| | | |
|---|---|---|
| 0328333 | 8/1989 | European Pat. Off. . |
| 0331483A2 | 9/1989 | European Pat. Off. . |
| 0342009A2 | 11/1989 | European Pat. Off. . |
| WO8905696 | 6/1989 | WIPO . |
| WO8907666 | 8/1989 | WIPO . |

OTHER PUBLICATIONS

"Epitaxial Film Growths of Artificial (Bi–O)/(Sr–Ca–Cu–O) Layers Structures," Fujita, J., et al., Appl. Phys. Lett., vol. 54, No. 23, Jun., 1989, pp. 2364–2366.

"High $T_c$ Oxide Superconductors," Maple, M.B., Ed., MRS Bulletin, Jan. 1989, pp. 20–21.

"Effect of Noble Metal Buffer Layers on Superconducting $Yba_2Cu_3O_7$ Thin Film," Appl. Phys. Lett., 1987, vol. 51, pp. 2155–2157, Chien et al.

(List continued on next page.)

*Primary Examiner*—Jose' G. Dees
*Assistant Examiner*—Dameron Jones
*Attorney, Agent, or Firm*—Steven J. Hultquist; Oliver A.M. Zitzmann

[57] ABSTRACT

A metalorganic complex of the formula:

$$MA_yX$$

wherein:

M is a y-valent metal;

A is a monodentate or multidentate organic ligand coordinated to M which allows complexing of MAY with X;

y is an integer having a value of 2, 3 or 4;

each of the A ligands may be the same or different; and

X is a monodentate or multidentate ligand coordinated to M and containing one or more atoms independently selected from the group consisting of atoms of the elements C, N, H, S, O and F.

The metal M may be selected from the group consisting of Cu, Ba, Sr, La, Nd, Ce, Pr, Sm, Eu, Th, Gd, Th, Dy, Ho, Er, Tm, Yb, Lu, Bi, Tl, Y, Pb, Ni, Pd, Pt, Al, Ga, In, Ag, Au, Co, Rh, Ir, Fe, Ru, Sn, Li, Na, K, Rb, Cs, Ca, Mg, Ti, Zr, Hf, V, Nb, Ta, Cr, Mo, and W. A may be selected from the group consisting of β-diketonates and their sulfur and nitrogen analogs, β-ketoesters and their sulfur and nitrogen analogs, cyclopentadienyls, alkyls, perfluoroalkyls, alkoxides, perfluoroalkoxides, and Schiff bases. X may for example comprise a ligand such as tetraglyme, tetrahydrofuran, bipyridine, crown ether, or thioether.

50 Claims, No Drawings

U.S. PATENT DOCUMENTS

| | | |
|---|---|---|
| 4,931,425 | 6/1990 | Kimura et al. . |
| 4,933,317 | 6/1990 | Johnston, Jr. et al. . |
| 4,935,385 | 6/1990 | Biegelsen . |
| 4,935,626 | 6/1990 | Schneider . |
| 4,937,225 | 6/1990 | Kalonji et al. . |
| 4,940,693 | 7/1990 | Shappirio et al. . |
| 4,943,558 | 7/1990 | Soltis et al. . |
| 4,943,559 | 7/1990 | Severin et al. . |
| 5,204,314 | 4/1993 | Kirlin et al. ................................. 505/1 |
| 5,225,561 | 7/1993 | Kirlin et al. ............................. 546/256 |
| 5,248,787 | 9/1993 | Timmer et al. . |
| 5,280,012 | 1/1994 | Kirlin et al. ................................. 505/1 |
| 5,453,494 | 9/1995 | Kirlin et al. ............................... 534/15 |
| 5,487,356 | 1/1996 | Li et al. ..................................... 117/99 |
| 5,504,195 | 4/1996 | Leedham et al. ......................... 534/15 |
| 5,536,323 | 7/1996 | Kirlin et al. ............................. 118/726 |
| 5,677,002 | 10/1997 | Kirlin et al. ......................... 427/248.1 |
| 5,786,025 | 7/1998 | Saitou et al. ............................... 427/99 |
| 5,820,664 | 10/1998 | Gardner et al. .................... 106/287.17 |
| 5,840,897 | 11/1998 | Kirlin et al. ................................. 546/2 |

OTHER PUBLICATIONS

"Suitability of Metal Beta–Diketonates as MOCVD–Precursors for High $T_c$ Superconductors," C.I.M.A. Spee, et al., TNO Institute of Applied Chemistry.

"Thin Films of Barium Fluoride Scintillator Deposited by Chemical Vapor Deposition," P.S. Kirlin, et al pp. 261–264.

"Growth of High $T_c$ YbaCuO Thin Films by Metalorganic Chemical Vapor Deposition," P.S. Kirlin, et al., SPIE vol. 1187, pp. 115–127.

"Superconductors Beyond 123," Cava, R.J., Sci. Amer., Aug., 1990, pp. 42–49.

"Reduced Pressure MOCVD of C–Axis Oriented BiSr-CaCuO Thin Films," Hamaguchi, N., Japanese Journal of Applied Physics, vol. 29, No. 4, Apr. 1990, L596–L599.

"A Study of Bis(Hexafluoroacetylacetonato) Copper (II)," Betrand, J.A., et al., Inorganic Chemistry, vol. 5, No. 3, Mar., 1966, pp. 489–491.

"Volatile Alkaline Earth Chelates of Fluorinate Alkanoylpivalylmethanes," Belcher, R., et al., Analytica Chem. Acta, 60 (1972) pp. 109–116.

"Microstructure and Properties of Superconducting Sputter Deposited Y–Ba–Cu–O Films," Kwasnick, R.F., et al., J. Mater. Res. vol., 4, No. 2, 1989, pp. 257–266.

"Fluorination of the High–$T_c$ Superconductors $YBa_2Cu_3O_7$–Δ," Sauer, N.N., et al. 1988, pp. 725–730.

"Solution Synthesis of Calcium, Strontium and Barium Metallocenes," McCormick, M.J., et al., Polyhedran, vol. 7, No. 9, 1988, pp. 725–730.

"A Review of Metal Organic Chemical Vapor Deposition of High–Temperature Superconducting Thin Film," Erbil, A., et al., SPIE vol. 1187, 1989, pp. 104–109.

"In–Situ Formation of Superconducting $YBa_2Cu_3O_{7-x}$ Thin Films using Pure Ozone Vapor Oxidation," Berkley, D.D., et al., Appl. Phys. Lett. vol. 53, No. 20, Nov. 1988, gs 1973–1975.

"In–Situ Processing of Epitaxial y–Ba–Cu–O High $T_c$ Superconducting Films on (100) $SrTiO_3$ and 9100) YS–Zr–$O_2$ Substrates at 500–650° C.,"Singh, R.k., et al., Appl. Phys. Lett. vol. 54, No. 22, May 1989, pp. 2271–2273.

"As–Grown Superconducting Bi–Sr–Ca–Cu–O Thin Films by Coevaporation," Yoshitake, T., et al., Appl. Phys. Lett., vol. 55, No. 7, Aug. 1989, pp. 702–704.

"Inorganic Scintillating Films and Optical Fibers Using CVD Films," Winn, D.R. et al. (unpublished).

"High $T_c$ Bismuth and Thallium Copper Oxide Superconductors," Sleight, A.W., et al., MRS Bulletin/Jan. 1989, pp. 45–48.

"Effect of the Post–Deposition Processing Ambient on the Preparation of Superconducting $YBa_2Cu_3O_{7-x}$ Coevaporated Thin Films Using a $BaF_2$ Source," Chan, S–W, et al., Appl. Phys. Lett., vol. 53, No. 15, Oct. 1988, pp. 1443–1445.

"A Few Comments on Superconducting AC Electric Machines," Keim, T.A., GE Research Center, pp. 147–149.

"MOCVD in Inverted Stagnation Point Flow," Journal of Crystal Growth, 77, 1986, pp. 120–127 (North–Holland) Lee et al.

"CVD in Stagnation Point Flow," Houtman, C., et al., Journal of the Electro Chem. Soc., May, 1986, pp. 961–970.

METAL COMPLEX SOURCE REAGENTS FOR CHEMICAL VAPOR DEPOSITION

CROSS-REFERENCE TO RELATED APPLICATIONS

This is a division of U.S. application Ser. No. 08/477,797 filed Jun. 7, 1995, now issued as U.S. Pat. No. 5,840,897, which is a continuation-in-part of U.S. application Ser. No. 08/181,800 filed Jan. 18, 1994, now issued as U.S. Pat. No. 5,453,494, which is a continuation-in-part of U.S. application Ser. No. 07/918,141 filed Jul. 22, 1992, now issued as U.S. Pat. No. 5,280,012, which is a continuation of U.S. application Ser. No. 07/615,303 filed Nov. 19, 1990, now abandoned, which is a divisional of U.S. application Ser. No. 07/581,631 filed Sep. 12, 1990, now issued as U.S. Pat. No. 5,225,561, which is a continuation-in-part of U.S. application Ser. No. 07/549,389 filed Jul. 6, 1990, now abandoned.

This also is a continuation-in-part of U.S. application Ser. No. 08/414,504 filed Mar. 31, 1995, now issued as U.S. Pat. No. 5,820,664, which is a continuation-in-part of U.S. application Ser. No. 08/280,143 filed Jul. 25, 1994, now issued as U.S. Pat. No. 5,536,323, which is a continuation of U.S. application Ser. No. 07/927,134 filed Aug. 7, 1992, now abandoned, which is a continuation-in-part of U.S. application Ser. No. 07/807,807 filed Dec. 13, 1991, now issued as U.S. Pat. No. 5,204,314, which is a continuation of U.S. application Ser. No. 07/549,389 filed Jul. 6, 1990, now abandoned.

BACKGROUND OF THE INVENTION

1. Field of the Invention

The present invention generally relates to thermally decomposable organometallic compounds and complexes which are useful in chemical vapor deposition (CVD) processes, for formation of metal films on substrates.

2. Description of the Related Art

Chemical vapor deposition is widely used for the formation of metal films on a variety of substrates. CVD is a particularly attractive method for forming metal films because it is readily scaled up to production runs and because the electronics industry has a wide experience and an established equipment base in the use of CVD technology which can be applied to CVD processes.

CVD requires source reagents which are sufficiently volatile to permit their gas phase transport into the decomposition reactor. The source reagent must decompose in the CVD reactor to deposit only the desired element(s) at the desired growth temperature on the substrate. Premature gas phase reactions are desirably avoided, and it generally is desired to controllably deliver source reagents into the CVD reactor to effect correspondingly close control of stoichiometry.

Many potentially useful metals do not form compounds which are well suited for CVD. Although some source reagents are solids which are amenable to sublimation for gas-phase transport into the CVD reactor, the sublimation temperature may be very close to decomposition temperature. Accordingly, the reagent may begin to decompose in the lines leading to the CVD reactor, and it then becomes difficult to control the stoichiometry of the deposited films.

Accordingly, there is a continuing search in the art for improved source reagent compositions which are amenable to vaporization to form the source component vapor for CVD processes, for applications such as the formation of diffusion barriers, conductors, dielectrics, protective coatings, phosphors, electroluminescent structures, ferroelectrics, giant magnetoresistive films, corrosion-resistant films, and mixed metal films.

In the chemical vapor deposition of multicomponent material systems, multiple source reagents are delivered to the CVD reactor. A particularly advantageous way of delivering multiple source reagents is to accurately mix neat liquid source reagents or liquid solutions of source reagents and then flash vaporize the mixture and deliver the resulting vapor to the reactor. It is possible in this situation for the reagents to undergo reactions, either in the liquid phase before vaporization or in the gas phase after vaporization. If these reactions convert a source reagent to an insoluble or non-volatile product, or to a material of different chemical or physical properties, then the elements contained in that product will not reach the substrate and the stoichiometry of the deposited film will be incorrect.

Examples of this problem (wherein Et is ethyl; tBu is tert-butyl; iPr is isopropyl; and thd is tetramethylheptanedionate) include the following:

(i) during deposition of $PbZr_xTi_{1-x}O_3$, using $(Et)_4Pb$, $Zr(OtBu)_4$, and $Ti(OiPr)_4$ source reagents, ligand exchange between the Zr and Ti reagents resulted in formation of $Zr(OiPr)_4$ (and perhaps other products of which $Zr(OiPr)_4$ is a monomer), which had very low volatility and which condensed in the gas manifold or vaporizer;

(ii) when solutions of $Ba(thd)_2$ and $Ti(OiPr)_4$ were mixed prior to vaporization, an insoluble precipitate was formed, presumably $Ba(OiPr)_2$; and (iii) when solutions of $Pb(thd)_2$ and $Ti(OiPr)_4$ were mixed in butyl acetate, the reagents reacted to form compounds of differing physical properties, such as $Pb(OiPr)_2$ and $Ti(OiPr)_2(thd)_2$.

Another specific example illustrating this problem is the preparation of films of strontium bismuth tantalate and strontium bismuth niobate ($SrBi_2Ta_2O_9$ and $SrBi_2Nb_2O_9$) by CVD for use in non-volatile ferroelectric random access memories. The most commonly used strontium source reagents are β-diketonate complexes such as $Sr(thd)_2$. When a solution is heated containing the following source reagents for deposition of $SrBi_2Ta_2O_9$:

$Sr(thd)_2$; $Ta(OEt)_5$; and $Bi(Ph)_3$ wherein Ph=phenyl, the ethoxide ligands of the tantalum reagent exchange with the thd ligands of the strontium reagent, leading to the formation of undesirable strontium alkoxide species that have reduced volatility and that can decompose in the vaporization zone. Alternatively, when these reagents are provided separately in bubblers, similar ligand exchange reactions occur in the gas phase; the resulting solids constrict the gas lines or alter the film stoichiometry.

In certain instances, such problems can be avoided by using identical ligands on the metals to make ligand exchange a degenerate reaction (i.e., where the exchanging ligand is identical to the original ligand). Examples of this approach include the use of tetraethylorthosilicate, triethylborate and triethylphosphite for deposition of borophosphosilicate glasses (*J. Electrochem. Soc.*, 1987, 134(2), 430). In many instances, however, this method for avoiding the problem is not possible because the appropriate compound does not exist, is too unstable or involatile to be used for CVD, or otherwise has disadvantageous physicochemical material properties. For example, for deposition of $PbZrxTi_{1-x}O_3$, a reagent system with identical ligands is problematic because while $Pb(thd)_2$ and $Zr(thd)_4$ are stable and volatile, $Ti(thd)_4$ does not exist and $Ti(thd)_3$ is extremely air sensitive. Similarly, while $Ti(OtBu)_4$ and $Zr(OtBu)_4$ are stable and volatile, $Pb(OtBu)_2$ is thermally unstable at temperatures required for volatilization.

The foregoing problems are also encountered in the circumstance where the metal source reagent is provided in a liquid solution and the solvent contains moieties which react with ligands of the source reagent compound to produce undesirable ligand exchange reaction by-products which display different physical properties and are involatile or insoluble.

Accordingly, it is an object of the present invention to provide improved metal source reagent compositions for the deposition of corresponding metals and metal oxides via CVD processes.

Other objects and advantages of the invention will be more fully apparent from the ensuing disclosure and appended claims.

SUMMARY OF THE INVENTION

The present invention generally relates to a metalorganic complex of the formula:

$$MA_yX$$

wherein:

M is a y-valent metal;

A is a monodentate or multidentate organic ligand coordinated to M which allows complexing of $MA_y$ with X;

y is an integer having a value of 2, 3 or 4;

each of the A ligands may be the same or different; and

X is a monodentate or multidentate ligand coordinated to M and containing one or more atoms independently selected from the group consisting of atoms of the elements C, N, H, S, O and F.

In such complex, M may for example be selected from the group consisting of Cu, Ba, Sr, La, Nd, Ce, Pr, Sm, Eu, Th, Gd, Th, Dy, Ho, Er, Tm, Yb, Lu, Bi, Tl, Y, Pb, Ni, Pd, Pt, Al, Ga, In, Ag, Au, Co, Rh, Ir, Fe, Ru, Sn, Li, Na, K, Rb, Cs, Ca, Mg, Ti, Zr, Hf, V, Nb, Ta, Cr, Mo, and W. The ligand A may be selected from the group consisting of β-diketonates and their sulfur and nitrogen analogs, β-ketoesters and their sulfur and nitrogen analogs, cyclopentadienyls, alkyls, perfluoroalkyls, alkoxides, perfluoroalkoxides, and Schiff bases. Specific examples of A include:

(i) 2,2,6,6-tetramethyl-3,5-heptanedionate;
(ii) 1,1,1,5,5,5-hexafluoro-2,4-pentanedionate;
(iii) 1,1,1,2,2,3,3-heptafluoro-7,7-dimethyl-4,6-octanedionate;
(iv) cyclopentadienyl;
(v) 4,4'-(ethane-1,2-diyldiimino) bis (3-pentene-2-one);
(vi) pentamethylcyclopentadienyl and other substituted cyclopentadienyls;
(vii) 2,4-pentanedionate; and
(viii) 1,1,1-trifluoro-2,4-pentanedionate.

The ligand X in such complexes may, for example, be selected from the group consisting of:

(i) oxyhydrocarbyl ligands;
(ii) nitrogenous oxyhydrocarbyl ligands;
(iii) fluorooxyhydrocarbyl ligands; and
(iv) thiooxyhydrocarbyl ligands.

Specific classes of X ligand species include:

(a) amines and polyamines;
(b) bipyridines;
(c) ligands of the formula:

wherein G is —O—, —S—, or —NR—, wherein R is H or hydrocarbyl;

(d) crown ethers;
(e) thioethers; and
(f) ligands of the formula:

$$R^0O(C(R^1)_2C(R^2)_2O)_nR^0$$

wherein:

$R^0$=H, methyl, ethyl, n-propyl, cyanato, perfluoroethyl, perfluoro-n-propyl, or vinyl;

$R^1$=H, F, or a sterically acceptable hydrocarbyl substituent;

$R^2$=H, F, or a sterically acceptable hydrocarbyl substituent;

n=2, 3, 4, 5, or 6; and each $R^0$, $R^1$, and $R^2$ may be the same as or different from the other $R^0$, $R^1$, and $R^2$, respectively.

Examples of such ligand X include tetraglyme, tetrahydrofuran, bipydridine, and 18-crown-6 ethers.

In the foregoing metalorganic complexes $MA_yX$, A is an organic ligand which is coordinative to M, which allows complexing of $MA_y$ with the ligand X, and which forms the sub-complex $MA_y$ with M which is stable, e.g., under standard temperature and pressure (STP) conditions (i.e., 25 degrees Centigrade, 1 atmosphere pressure), and thus may be referred to as a "stable STP sub-complex $MA_y$."

In a more specific aspect, the ligand X may have the formula:

$$R^0O(C(R^1)_2(R^2)_2O)_nR^0$$

wherein:

$R^1$=H, methyl, ethyl, n-propyl, cyanato, perfluoroethyl, perfluoro-n-propyl, or vinyl;

$R^1$=H, F, or a sterically acceptable hydrocarbyl substituent;

$R^2$=H, F, or a sterically acceptable hydrocarbyl substituent;

n=2, 3, 4, 5, or 6; and each $R^0$, $R^1$, and $R^2$ may be the same as or different from the other $R^0$, $R^1$, and $R^2$, respectively.

In a further specific aspect, the ligand X may have the formula:

$$R^0O(C(R^1)_2C(R^2)_2O)_4R^0$$

wherein:

each $R^0$, $R^1$, and $R^2$ is selected independently, and $R^0$=H, $CH_3$, or $C_2H_5$;

$R^1$ and $R^2$=H or F.

In the metalorganic complexes described above, each of the ligands A may be a constituent moiety of a single group which is coordinatingly attached to M thereby. Alternatively, the ligand X and at least one of the ligands A may be a constituent moiety of a single group which is coordinatingly attached to M thereby.

In use, for the formation of metal or metal oxide films on a substrate, the metalorganic complexes of the invention may be employed in a solvent or suspending agent for the complex(es), to thereby form a metal source reagent solution comprising the metalorganic complex(es) and the solvent or suspending agent. Such metal source reagent liquid solution may then be volatilized to yield a metal source vapor, and the metal source vapor may be contacted with a substrate in a CVD reactor, to deposit the metal-containing film on the substrate.

In another aspect, the invention relates to a metalorganic composition comprising:

(i) a metalorganic complex of the formula:

$$MA_yX$$

wherein:

M is a y-valent metal;

A is a monodentate or multidentate organic ligand coordinated to M which allows complexing of $MA_y$ with X;

y is an integer having a value of 2, 3 or 4;

each of the A ligands may be the same or different; and

X is a monodentate or multidentate ligand coordinated to M and containing one or more atoms independently selected from the group consisting of atoms of the elements C, N, H, S, O and F, or precursor(s) or components thereof; and (ii) a solvent or suspending agent therefor.

The composition may for example comprise the components of the metalorganic complex in a solvent, wherein the components react in situ in the solvent to form the metalorganic complex. In like manner, the composition may comprise precursors of the metalorganic complex in the solvent, wherein the precursors react in situ in the solvent to form the metalorganic complex. Similar compositions may be formed in which the metalorganic complex is not soluble in a liquid medium, but is suspendible or dispersible therein, whereby the liquid functions as a suspending agent for the complex.

In another aspect, the invention relates to a metalorganic complex of the formula:

$$M_1M_2A_yX$$

wherein:

$M_1$ is a metal of valence n;

$M_2$ is a metal of valence y-n;

$M_1$ and $M_2$ are different from one another;

A is a monodentate or multidentate organic ligand coordinated to at least one of $M_1$ and $M_2$ which allows complexing of $M_1M_2A_y$ with X;

n is an integer having a value of 1, 2 or 3;

y is an integer having a value of 2, 3 or 4, and y>n;

each of the A ligands may be the same or different; and

X is a monodentate or multidentate ligand coordinated to at least one of $M_1$ and $M_2$ and containing one or more atoms independently selected from the group consisting of atoms of the elements C, N, H, S, O and F.

Each of $M_1$ and $M_2$ in the metalorganic complex may be independently selected from the group consisting of Cu, Ba, Sr, La, Nd, Ce, Pr, Sm, Eu, Tb, Gd, Th, Dy, Ho, Er, Tm, Yb, Lu, Bi, Tl, Y, Pb, Ni, Pd, Pt, Al, Ga, In, Ag, Au, Co, Rh, Ir, Fe, Ru, Sn, Li, Na, K, Rb, Cs, Ca, Mg, Ti, Zr, Hf, V, Nb, Ta, Cr, Mo, and W.

In a preferred aspect, $M_1$ and $M_2$ are selected from the group of $M_1$/$M_2$ pairs consisting of:

| | $M_1$ | $M_2$ |
|---|---|---|
| (i) | Cu | Sn; |
| (ii) | Cu | In; |
| (iii) | Al | Cu; |
| (iv) | Fe | Mn; |
| (v) | Fe | Ni; and |
| (vi) | Fe | Co. |

Still another method aspect of the invention relates to a metal source reagent solution, which comprises:

(i) at least one metal coordination complex including a metal to which is coordinatively bound at least one ligand in a stable complex, wherein the ligand is selected from the group consisting of: β-diketonates, β-thioketonates, β-ketoiminates, β-diiminates, $C_1$–$C_8$ alkyl, $C_2$–$C_{10}$ alkenyl, $C_2$–$C_{15}$ cycloalkenyl, $C_6$–$C_{10}$ aryl, $C_1$–$C_8$ alkoxy, and fluorinated derivatives thereof; and (ii) a solvent for the metal coordination complex.

The metal in the metal coordination complex(es) employed in the above-discussed method may comprise a metal selected from the group consisting of: Mg, Ca, Sr, Ba, Sc, Y, La, Ce, Ti, Zr, Hf, Pr, V, Nb, Ta, Nd, Cr, W, Pm, Mn, Re, Sm, Fe, Ru, Eu, Th, Lu, Pd, Pt, Ga, In, Au, Ag, Li, Na, K, Rb, Cs, Mo, Co, Rh, Ir, Gd, Ni, Tb, Cu, Dy, Ho, Al, Tl, Er, Sn, Pb, Tm, Bi, and Yb. The metal source reagent liquid solution may in some instances comprise a multi-component solution including at least two of the aforementioned metal source complexes. The metal source reagent liquid solution may include solvent species selected such as: glymes, aliphatic hydrocarbons, aromatic hydrocarbons, ethers, esters, nitriles, and/or alcohols. The solvent may, for example, comprise at least one solvent species selected from the group of solvents consisting of: glyme solvents having from 1 to 20 ethoxy —($C_2H_4O$) repeat units; $C_2$–$C_{12}$ alkanols, organic ethers selected from the group consisting of dialkyl ethers comprising $C_1$–$C_6$ alkyl moieties, $C_4$–$C_8$ cyclic ethers, and $C_{12}$–$C_{60}$ crown $O_4$–$O_{20}$ ethers wherein the prefixed $C_i$ range is the number i of carbon atoms in the ether compound and the suffixed $O_i$ range is the number i of oxygen atoms in the ether compound; $C_6$–$C_{12}$ aliphatic hydrocarbons; and $C_6$–$C_{18}$ aromatic hydrocarbons.

In yet a further aspect, the present invention relates to a metal source reagent solution including a metal source reagent and solvent medium, which is volatilizable to yield a metal source vapor for contacting with a substrate, to deposit a metal-containing film thereon, wherein the metal source reagent(s) and the solvent medium are selected from the group, set out in Table I below, of metal source reagent(s) and associated solvent media consisting of:

TABLE I

| Metal Source Reagent(s) | Solvent Medium |
|---|---|
| Al(thd)$_3$ | 80–98% tetrahydrofuran and 2–20% tetraglyme |
| Al(OR)$_3$ | 80–98% tetrahydrofuran and 2–20% tetraglyme |
| Ba(thd)$_2$(tetraglyme) | 85–99% butyl acetate and 1–15% tetraglyme |
| Ca(thd)$_2$(tetraglyme) | |
| Cu(thd)$_2$ | |
| Ba(thd)$_2$(tetraglyme) | 85–98% butyl acetate and 1–15% tetraglyme |
| Sr(thd)$_2$(tetraglyme) | |
| Ti(OiPr)$_2$(thd)$_2$ | |

TABLE I-continued

| Metal Source Reagent(s) | Solvent Medium |
|---|---|
| Ca(thd)$_2$(tetraglyme) | 75–95% isopropanol with 5–25% tetraglyme |
| Sr(thd)$_2$(tetraglyme) | |
| Cr(thd)$_3$ | 80–98% tetrahydrofuran with 2–20% tetraglyme |
| Er(thd)$_3$ | 85–99% butyl acetate and 1–15% tetraglyme |
| Ir(acac)$_3$ or Ir(thd)$_3$ | butyl acetate |
| La(thd)$_3$ (MeO)$_3$P = O | tetrahydrofuran |
| MgAl(OiPr)$_8$ | isopropanol |
| Nb(OiPr)$_4$thd | 45–88% tetrahydrofuran 10–35% isopropanol 2–20% tetraglyme |
| Pb(thd)$_2$ | 80–98% tetrahydrofuran and 2–20% tetraglyme |
| La(thd)$_3$ Ti(OiPr)$_2$(thd)$_2$ Pb(thd)$_2$ | 80–98% tetrahydrofuran with 2–20% tetraglyme |
| Ti(OiPr)$_2$thd$_2$ Pb(thd)$_2$ Zr(thd)$_4$ | 45–88% tetrahydrofuran 10–35% isopropanol 2–20% tetraglyme |
| Pb(thd)$_2$ Zr(thd)$_4$ Ti(OiPr)$_2$(thd)$_2$ | 45–88% tetrahydrofuran 10–35% isopropanol 2–20% tetraglyme |
| Ru(acac)$_3$ or Ru(thd)$_3$ | butyl acetate |
| Sn (alkyl)$_2$ (β-diketonate)$_2$ wherein alkyl = C$_1$–C$_{18}$ alkyl | butyl acetate |
| Sn (acetate)$_2$ | butyl acetate or 85–99% butyl acetate and 1–15% tetraglyme |
| Sr(thd)$_2$(tetraglyme) BiPh$_3$ Ta(OiPr)$_4$(thd) | 45–88% tetrahydrofuran 10–35% isopropanol 2–20% tetraglyme |
| Ta(OEt)$_5$ | 1% ethanol solution |
| [O = Ti(thd)$_2$]$_n$ wherein n is 1 or 2 | butyl acetate |
| Zr(thd)$_4$ | 80–98% tetrahydrofuran and 2–20% tetraglyme |
| Y(thd)$_3$ [O = Zr(thd)$_2$]$_n$ wherein n is 1 or 2 | butyl acetate |
| Y(thd)$_3$ | or butyl acetate/tetraglyme isopropanol |
| Y(thd)$_3$ Ba(thd)$_2$ Cu(thd)$_2$ | butyl acetate/tetraglyme |
| Cu(shfac)$_2$ | 85–99% butyl acetate and 1–15% tetraglyme |
| Sr(shfac)$_2$ | 85–99% butyl acetate and 1–15% tetraglyme |
| Sr(sthd)$_2$ | 85–99% butyl acetate and 1–15% tetraglyme |
| Sr(sthd)$_2$ | 85–99% butyl acetate and 1–15% tetrathiocyclodecane |
| Ca(sthd)$_2$ Sr(sthd)$_2$ Ga(sthd)$_3$ Ce(sthd)$_4$ | 85–99% butyl acetate and 1–15% tetraglyme |
| Ca(sthd)$_2$ Ga(sthd)$_3$ Ce(sthd)$_4$ | 85–99% butyl acetate and 1–15% tetraglyme |
| Ca(sthd)$_2$ Sr(sthd)$_2$ Ga(sthd)$_3$ Ce(sthd)$_4$ | 85–99% butyl acetate and 1–15% tetrathiocyclodecane |
| Cu(shfac)$_2$ | 45–88% tetrahydrofuranacetate 10–35% isopropanol 2–20% tetraglyme |
| Cu(hfac)$_2$ | 85–99% butyl acetate and 1–15% tetraglyme |
| Sr(thd)$_2$ | 85–99% butyl acetate and 1–15% tetraglyme |
| Sr(thd)$_2$ | 85–99% butyl acetate and 1–15% tetrathiocyclodecane |
| Cu(hfac)$_2$ | 45–88% tetrahydrofuranacetate 10–35% isopropanol 2–20% tetraglyme |
| Ti(hfac)$_3$ | 85–99% butyl acetate and 1–15% tetraglyme |
| Ti(hfac)$_3$ | butyl acetate |
| Mo(hfac)$_3$ | butyl acetate |
| Mo(thd)$_3$ | butyl acetate | wherein when the solvent medium contains multiple solvent components, the percentages specified are percentages by weight, based on the weight of the total solvent medium, and with the total percentage of all solvent components being 100%.

A further aspect of the invention relates to sulfur-based complexes having utility for forming a metal sulfide film on a substrate, comprising sulfur-containing metal source reagent compounds in a solvent medium, in which the sulfur-containing metal source reagent may complex with a suitable ligand deriving from the solvent medium. Illustrative sulfur-containing metal source compounds and appertaining solvent media, are set out in Table II below.

TABLE II

| Metal Source Compound | Solvent Medium |
|---|---|
| Cu(shfac)$_2$ | 85–99% butyl acetate and 1–15% tetraglyme |
| Sr(shfac)$_2$ | 85–99% butyl acetate and 1–15% tetraglyme |
| Sr(sthd)$_2$ | 85–99% butyl acetate and 1–15% tetraglyme |
| Sr(sthd)$_2$ | 85–99% butyl acetate and 1–15% tetrathiocyclodecane |
| Ca(sthd)$_2$ Sr(sthd)$_2$ Ga(sthd)$_3$ Ce(sthd)$_4$ | 85–99% butyl acetate and 1–15% tetraglyme |
| Ca(sthd)$_2$ Ga(sthd)$_3$ Ce(sthd)$_4$ | 85–99% butyl acetate and 1–15% tetraglyme |
| Ca(sthd)$_2$ Sr(sthd)$_2$ Ga(sthd)$_3$ Ce(sthd)$_4$ | 85–99% butyl acetate and 1–15% tetrathiocyclodecane |
| Cu(shfac)$_2$ | 45–88% tetrahydrofuran 10–35% isopropanol 2–20% tetraglyme |

The volatilization of the above-identified sulfur-containing metal source compounds from the solution creates a metal source vapor which may be delivered (transported) to a CVD reactor, for deposition of the metal on the substrate in the form of a sulfide. Such deposition of the metal on the substrate may be carried out in the presence of a sulfur-containing gas, e.g., a sulfur-containing gas selected from the group of sulfur compounds consisting of hydrogen sulfide, t-butyl thiol, and cyclohexyl thiol.

Alternatively, a source compound not containing sulfur, such as those identified in Table III below, may be contacted with a substrate under CVD conditions, and in the presence of a sulfur compound or component, to form a metal sulfide film on the substrate.

TABLE III

| Metal Source Compound | Solvent Medium |
| --- | --- |
| $Cu(hfac)_2$ | 85–99% butyl acetate and 1–15% tetraglyme |
| $Sr(thd)_2$ | 85–99% butyl acetate and 1–15% tetraglyme |
| $Sr(thd)_2$ | 85–99% butyl acetate and 1–15% tetrathiocyclodecane |
| $Cu(hfac)_2$ | 45–88% tetrahydrofuran 10–35% isopropanol 2–20% tetraglyme |
| $Ti(hfac)_3$ | 85–99% butyl acetate and 1–15% tetraglyme |
| $Ti(hfac)_3$ | butyl acetate |
| $Mo(hfac)_3$ | butyl acetate |
| $Mo(thd)_3$ | butyl acetate. |

The sulfur constituent in such formation of a metal sulfide film may for example comprise a sulfur-containing component in the solvent phase of the precursor source composition, such as hydrogen sulfide. Alternatively, the sulfur constituent required to form the metal sulfide film may be introduced in the vapor phase during the CVD metal film deposition process, whereby the vapor phase sulfur combines with the metal film being formed on the substrate, yielding the desired metal sulfide film.

Such metal sulfide films may have utility in the fabrication of display phosphor screens or detector, and metal sulfide films because of their lubricious character, have potential utility in a wide variety of tribological applications, as wear inhibitor films.

Compositions according to the invention, comprising a metal source reagent solution including a metal β-thioketonate source reagent and a compatible solvent medium for the metal β-thioketonate source reagent, may be employed for directly forming a metal sulfide film on a substrate. The metal moiety of the metal β-thioketonate source reagent may be a metal such as Cu, Sr, Ca, Ga, Ce, Ti, and Mo. By volatilizing the metal source reagent liquid solution to yield a metal source vapor, and contacting the metal source vapor with the substrate, a metal sulfide film may be advantageously deposited on the substrate. Such contacting of the metal source vapor with the substrate may advantageously be carried out in the presence of hydrogen sulfide or other sulfur source gas or component, such as t-butylthiol, or cyclohexylthiol, to enhance the efficacy of the metal sulfide film formation.

Alternatively, a metal sulfide film may be formed on a substrate via CVD processing, wherein a metal source reagent whose metal moiety is reactive with sulfur to form a metal sulfide film, is deposited on a substrate in the presence of hydrogen sulfide vapor, or other sulfur-containing vapor, to form the metal sulfide film. As a still further alternative, a metal source reagent in accordance with the invention may be provided in a liquid solution containing a sulfur constituent, e.g., hydrogen sulfide, t-butylthiol and cyclohexyl thiol, whereby the volatilization of the reagent solution results in the formation of a metal sulfide film.

As an example of the use of metal reagent compositions in accordance with the invention, for forming a metal-containing film on a substrate, a listing is set out in Table IV below of illustrative compositions of metal-containing films, together with corresponding metal source reagent and solvent medium species, which may be employed in the formation of such metal and metal oxide films. It will be recognized that in some instances of the compositions set out in the Table, the solvent species, e.g., tetraglyme, may advantageously complex in situ with the metal source compound, to form a stabilized complex, which facilitates highly efficient deposition of the metal deposition species from the resulting complex.

TABLE IV

| Metal Containing Film | Metal Source Reagent | Solvent Medium |
| --- | --- | --- |
| $Al_2O_3$ | $Al(thd)_3$ | tetrahydrofuran/tetraglyme |
| $Al_2O_3$ | $Al(OR)_3$ | tetrahydrofuran/tetraglyme |
| BaCaCuO | $Ba(thd)_2(tetraglyme)$, $Ca(thd)_2$, $Cu(thd)_2$ | butyl acetate/tetraglyme |
| $Ba_xSr_{1-x}TiO_3$ x = 0 to 1 | $Ba(thd)_2(tetraglyme)$ $Sr(thd)_2(tetraglyme)$ $Ti(OiPr)_2(thd)_2$ | butyl acetate/tetraglyme |
| BiSrCaCuO | $Sr(thd)_2(tetraglyme)$ $Ca(thd)_2(tetraglyme)$ $Bi(C_6H_5)_3$ $Cu(thd)$ | isopropanol/tetraglyme; |
| $Cr_2O_3$ | $Cr(thd)_3$ | tetrahydrofuran/tetraglyme; |
| Er doping of $SiO_2$ | $Er(thd)_3$ | butyl acetate/tetraglyme |
| Ir | $Ir(acac)_3$ or $Ir(thd)_3$ | butyl acetate |
| $LaPO_4$ | $La(thd)_3$ $O = P(OMe)_3$ | tetrahydrofuran |
| $MgAl_2O_4$ | $MgAl_2(OiPr)_8$ | isopropanol |
| $Nb_2O_5$ | $Nb(OiPr)_4(thd)$ | tetrahydrofuran/isopropanol/tetraglyme |
| $PbLa_xTi_{1-x}O_3$ | $Pb(thd)_2$ $La(thd)_3$ $Ti(OiPr)_2(thd)_2$ | tetrahydrofuran/tetraglyme |
| $PbTiO_3$ | $Pb(thd)_2$ $Ti(OiPr)_2(thd)_2$ | tetrahydrofuran/tetraglyme |
| $PbZrO_3$ | $Pb(thd)_2$ $Zr(thd)_4$ | tetrahydrofuran/isopropanol/tetraglyme |
| $PbZr_xTi_{1-x}O_3$ x = 0 to 1 | $Pb(thd)_2$ $Zr(thd)_4$ $Ti(OiPr)_2(thd)_2$ | tetrahydrofuran/isopropanol/tetraglyme |
| $PbZr_xTi_{1-x}O_3$ x = 0 to 1 | $Pb(thd)_2$ $[O = Zr(thd)_2]_n$ $[O = Ti(thd)_2]_n$ n = 1 or 2 | tetrahydrofuran/isopropanol/tetraglyme, or butyl acetate/tetraglyme |
| $RuO_2$ | $Ru(acac)_3$ or $Ru(thd)_3$ | butyl acetate |
| $SnO_2$ | $Sn(alkyl)_2$ (β-diketonate)$_2$ alkyl = $C_1$—$C_{18}$ | butyl acetate |
| $SnO_2$ | Sn (acetate)$_2$ | butyl acetate |
| $SrBi_2Ta_2O_9$ | $Sr(thd)_2$ tetraglyme $BiPh_3$ $Ta(OiPr)_4thd$ | tetrahydrofuran/isopropanol/tetraglyme |
| $Ta_2O_5$ | $Ta(OEt)_5$ | ethanol |
| $Ta_2O_5$ | $Ta(OR)_4(thd)$ R = ethyl, isopropyl | tetrahydrofuran/isopropanol/tetraglyme |
| $TiO_2$ | $[O = Ti(thd)_2]_n$ n = 1 or 2 | butyl acetate/tetraglyme |
| $V_2O_5$ | $O = V(thd)_3$ | butyl acetate/tetraglyme. |
| $Y_2O_3$—$ZrO_2$ | $Zr(thd)_4$ $Y(thd)_3$ | tetrahydrofuran/tetraglyme; |
| $Y_2O_3$ | $Y(thd)_3$ | isopropanol |
| YBaCuO | $Y(thd)_3$ $Ba(thd)_2(tetraglyme)$ $Cu(thd)_2$ | butyl acetate/tetraglyme or tetraglyme |
| $ZrO_2$ | $[O = Zr(thd)_2]_n$ n = 1 or 2 | butyl acetate/tetraglyme |
| CuS | $Cu(shfac)_2$ | butyl acetate/tetraglyme |
| SrS | $Sr(shfac)_2$ | butyl acetate/tetraglyme |

TABLE IV-continued

| Metal Containing Film | Metal Source Reagent | Solvent Medium |
| --- | --- | --- |
| SrS | Sr(sthd)$_2$ | butyl acetate/ tetraglyme |
| SrS | Sr(sthd)$_2$ | butyl acetate/ tetrathiocyclodecane |
| (Ca, Sr)Ga$_2$S$_4$, cerium-doped | Ca(sthd)$_2$ Sr(sthd)$_2$ Ga(sthd)$_3$ Ce(sthd)$_4$ | butyl acetate/ tetraglyme |
| (Ca, Sr)Ga$_2$S$_4$, cerium-doped | Ca(sthd)$_2$ Sr(sthd)$_2$ Ga(sthd)$_3$ Ce(sthd)$_4$ | butyl acetate/ tetrathiocyclodecane |
| CuS | Cu(shfac)$_2$ | tetrahydrofuranacetate isopropanol tetraglyme |
| CuS | Cu(hfac)$_2$ | butyl acetate/ tetraglyme |
| SrS | Sr(thd)$_2$ | butyl acetate/ tetraglyme |
| SrS | Sr(thd)$_2$ | butyl acetate/ tetrathiocyclodecane |
| CuS | Cu(hfac)$_2$ | tetrahydrofuranacetate isopropanol tetraglyme |
| TiS$_2$ | Ti(hfac)$_3$ | butyl acetate/ tetraglyme |
| TiS$_2$ | Ti(hfac)$_3$ | butyl acetate |
| MoS$_2$ | Mo(hfac)$_3$ | butyl acetate |
| MoS$_2$ | Mo(thd)$_3$ | butyl acetate. |

As an extension of the above-discussed method for forming a metal sulfide film on a substrate, the metal sulfide film may advantageously be reacted with a metal-coreactant to form a binary metal sulfide film on the substrate, e.g., CuInS, CuGaS, CuSeS, etc.

In a specific aspect of the present invention, metal-organic source reagent-containing liquid compositions employed to carry out the chemical vapor deposition (CVD) process are advantageously stabilized in character, meaning that the metal-organic source reagent therein is resistant to degradation via ligand exchange reactions, e.g., non-degenerative ligand exchanges which adversely affect the chemical identity and suitability of the reagent compositions for CVD applications.

Such metal source reagent liquid solutions may for example comprise:

(i) at least one metal coordination complex, each of such metal coordination complexes including a metal coordinatively binding at least one ligand in a stable complex, wherein such at least one ligand is selected from the group consisting of β-diketonates and β-ketoesters, and their sulfur and nitrogen analogs (i.e., corresponding ligands containing S or N atoms in place of the O atom(s) in the β-diketonates and β-ketoesters); and (ii) a solvent for such metal coordination complex(es).

A generalized formula for each of such metal coordination complexes is

$$M^iA_a(OR)_xB_yQ_z$$

wherein:

M is a metal selected from the group consisting of Mg, Ca, Sr, Ba, Sc, Y, La, Lu, Ce, Ti, Zr, Hf, Pr, V, Nb, Ta, Nd, Cr, W, Pm, Mn, Re, Sm, Fe, Ru, Eu, Co, Rh, Ir, Gd, Ni, Th, Th, Cu, Dy, Ho, Al, Tl, Er, Sn, Pb, Pd, Pt, Ga, In, Au, Ag, Li, Na, K, Rb, Cs, Mo, Tm, Bi, and Yb;

A is selected from the group consisting of β-diketonates and β-ketoesters, and their sulfur and nitrogen analogs;

R is selected from the group consisting of $C_1$–$C_8$ alkyl, $C_2$–$C_8$ cycloalkyl, $C_2$–$C_{10}$ alkenyl, $C_2$–$C_{15}$ cycloalkenyl, $C_6$–$C_{10}$ aryl, and (fully or partially) fluorinated derivatives thereof (i.e., wherein hydrogen substituent(s) of the $C_1$–$C_8$ alkyl, $C_2$–$C_8$ cycloalkyl, $C_2$–$C_{10}$ alkenyl, $C_2$–$C_{15}$ cycloalkenyl, or $C_6$–$C_{10}$ aryl ligand, is/are replaced by fluorine substituent(s));

B is selected from the group consisting of polyethers, polyamines, polythiols, bipyridines, glymes, alcohols, crown ethers, crown thioethers, cyclic polyamines (cyclenes), thioglymes, arylthiols, and aliphatic thiols (mercaptans).

Q is hydrocarbyl or halohydrocarbyl, e.g., a ligand selected from the group consisting of $C_1$–$C_8$ alkyl, $C_2$–$C_8$ cycloalkyl, $C_2$–$C_{10}$ alkenyl, $C_2$–$C_{15}$ cycloalkenyl, $C_6$–$C_{10}$ aryl, and fluorinated derivatives thereof;

a, x, y, and z are stoichiometric coefficients for the ligands A, OR, B, and Q, respectively, wherein a is $\geq 1$; each of x, y, and z is independently $\geq 0$; and $A_a(OR)_xB_yQ_z$ is in stoichiometric relationship to metal M.

Thus, each of the metal complexes in such solutions comprises at least one ligand A coordinated to the central atom M of the complex, and M may optionally have additionally coordinated thereto one or more of the ligands OR, B, and Q, in which the resulting complex is appropriately stoichiometrically constituted to define a stable complex.

One class of source reagent complexes usefully employed in reagent solutions in the process of the invention comprise those of the formula:

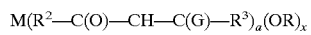

$$M(R^2-C(O)-CH-C(G)-R^3)_a(OR)_x$$

wherein:

a, x, M and R are as defined hereinabove;

$R^2$ and $R^3$ are independently selected from $C_1$–$C_8$ alkyl, $C_2$–$C_8$ cycloalkyl, $C_2$–$C_{10}$ alkenyl, $C_2$–$C_{15}$ cycloalkenyl, $C_6$–$C_{10}$ aryl, and fluorinated derivatives thereof; and G is oxygen, sulfur, or nitrogen moiety of the formula $=NR_b$ in which $R_b$ is selected from the group consisting of H, $C_1$–$C_8$ alkyl, $C_2$–$C_8$ cycloalkyl, $C_2$–$C_{10}$ alkenyl, $C_2$–$C_{15}$ cycloalkenyl, $C_6$–$C_{10}$ aryl, and fluorinated derivatives thereof.

The solvent utilized in the source reagent solutions in the process of the invention may comprise any suitable solvent species, or combination of solvent species, with which the metal complexes are compatible, such as aliphatic hydrocarbons, aromatic hydrocarbons, ethers, esters, nitrites, and alcohols. The solvent component of the solution preferably comprises a solvent selected from the group consisting of: glyme solvents having from 1 to 20 ethoxy —$(C_2H_4O)$— repeat units; $C_2$–$C_{12}$ alkanols, organic ethers selected from the group consisting of dialkyl ethers comprising $C_1$—$C_6$ alkyl moieties, $C_4$–$C_8$ cyclic ethers; $C_{12}$—$C_{60}$ crown $O_4$–$O_{20}$ ethers wherein the prefixed $C_i$ range is the number i of carbon atoms in the ether compound and the suffixed $O_i$ range is the number i of oxygen atoms in the ether compound; $C_6$–$C_{12}$ aliphatic hydrocarbons; $C_6$–$C_{18}$ aromatic hydrocarbons; organic esters; organic amines; and polyamines.

As used herein, the term "stable complex" means that the metal source complex in a pure state (unexposed to other materials, such as water, oxygen, etc.) is not susceptible to spontaneous degradation or decomposition at 25 degrees Centigrade and 1 atmosphere pressure. The term "complex" is intended to be broadly construed to encompass compounds as well as coordination complexes wherein at least one metal atom is coordinated (covalently, ionically and/or associatively) to at least one organic ligand group.

In yet another aspect, the source reagent compositions of the invention may comprise:

(i) at least one, and preferably at least two, metal coordination complexes, each of the formula:

$$M^iA_a(OR)_xB_yQ_z$$

wherein:

M is a metal selected from the group consisting of Mg, Ca, Sr, Ba, Sc, Y, La, Ce, Ti, Zr, Hf, Pr, V, Nb, Ta, Nd, Cr, W, Pm, Mn, Re, Sm, Fe, Ru, Eu, Co, Rh, Ir, Gd, Nit Tb, Cu, Dy, Ho, Al, Tl, Er, Sn, Pb, Tm, Bi, Lu, Th, Pd, Pt, Ga, In, Au, Ag, Li, Na, K, Rb, Cs, Mo, and Yb;

A is selected from the group consisting of β-diketonates and β-ketoesters, and their sulfur and nitrogen analogs;

R is selected from the group consisting of $C_1$–$C_8$ alkyl, $C_2$–$C_8$ cycloalkyl, $C_2$–$C_{10}$ alkenyl, $C_2$–$C_{15}$ cycloalkenyl, $C_6$–$C_{10}$ aryl, and (fully or partially) fluorinated derivatives thereof (i.e., wherein hydrogen substituent(s) of the $C_1$–$C_8$ alkyl, $C_2$–$C_8$ cycloalkyl, $C_2$–$C_{10}$ alkenyl, $C_2$–$C_{15}$ cycloalkenyl, or $C_6$–$C_{10}$ aryl ligand, is/are replaced by fluorine substituent(s));

B is selected from the group consisting of polyethers, polyamines, polythiols, bipyridines, glymes, alcohols, crown ethers, crown thioethers, cyclic polyamines (cyclenes), thioglymes, arylthiols, and aliphatic thiols (mercaptans).

Q is hydrocarbyl or halohydrocarbyl, e.g., a ligand selected from the group consisting of $C_1$–$C_8$ alkyl, $C_2$–$C_8$ cycloalkyl, $C_2$–$C_{10}$ alkenyl, $C_2$–$C_{15}$ cycloalkenyl, $C_6$–$C_{10}$ aryl, and fluorinated derivatives thereof;

a, x, y, and z are stoichiometric coefficients for the ligands A, OR, B, and Q, respectively, wherein a is 1; each of x, y, and z is independently $\geq 0$, and $A_a(OR)_xB_yQ_z$ is in stoichiometric relationship to metal M; and (ii) a solvent for the metal coordination complex(es).

The solution compositions of the invention may include compounds comprised of β-diketonate and/or alkoxide ligands having a metal M, e.g., selected from the group consisting of Mg, Ca, Sr, Ba, Sc, Y, La, Ce, Ti, Zr, Hf, Pr, V, Nb, Ta, Nd, Cr, W, Pm, Mn, Re, Sm, Fe, Ru, Eu, Co, Rh, Ir, Gd, Ni, Th, Cu, Dy, Ho, Al, Ti, Er, Sn, Pb, Tm, Bi, Lu, Th, Pd, Pt, Ga, In, Au, Ag, Li, Na, K, Rb, Cs, Mo, and Yb, complexed to at least one alkoxide ligand and at least one βdiketonate ligand.

Such compounds may have the general formula:

$$M(OR^1)_x(R^2-C(G)-CH-C(G)-R^3)_y$$

wherein:

G is oxygen, sulfur, or imide of the formula: $=NRb$, wherein $R_b$ is H, $C_1$–$C_8$ alkyl, or $C_1$–$C_8$ perfluoroalkyl (e.g., trifluoroethyl);

x+y=p where p is the valence of metal M;

x+2y=q where q is the coordination number of the metal M;

$R^1$ is $C_1$–$C_6$ hydrocarbyl or fluoroalkyl;

$R^2$ and $R^3$ are independently selected from $C_1$–$C_{14}$ hydrocarbyl, $C_1$–$C_6$ alkoxy, and $C_2$–$C_6$ fluoroalkyl groups, wherein hydrocarbyl groups may be selected from $C_1$–$C_8$ alkyl, $C_6$–$C_{10}$ cycloalkyl, $C_2$–$C_{12}$ alkenyl and $C_6$–$C_{14}$ aryl groups, and $C_1$–$C_6$ fluoroalkyl groups may be selected from perfluoroalkyls of 2 through 6 carbons.

As used herein, the following terms for ligand groups have the following meanings: acac=acetylacetonate, more specifically 2,4-pentane dionate; hfacac (or hfac)= hexafluoroacetylacetonate, more specifically 1,1,1,5,5,5-hexafluoro-2,4-pentanedionate; tfacac (or tfac)= trifluoroacetylacetonate, more specifically 1,1,1-trifluoro-2,4-pentanedionate; thd=tetramethylheptanedionate, as hereinabove identified, and more specifically 2,2,6,6-tetramethyl-3,5-heptanedionate; fod= fluorodimethyloctanedionate, more specifically 1,1,1,2,2,3,3-heptafluoro-7,7-dimethyl-4,6-octanedionate; hfod= heptafluoro-dimethyloctanedionate; and tg=tetraglyme. The corresponding β-thioketonate ligands are identified consistently therewith, by prefixation of "s" to the corresponding β-diketonate ligand, e.g., shfac, sthd, etc.

When identified herein by reference to generalized formulas, the copper oxide compound formulas YBaCuO, BaCaCuO, and BiSrCaCuO are intended to be construed to encompass the corresponding stoichiometrically appropriate specific stoichiometries (i.e., specific stoichiometric coefficients w, x, y, and z) of the metal moieties, in relation to the other metal components and the oxygen constituent of such compounds, that yield stable forms of the metal oxide compounds at 25° C. and 1 atmosphere pressure. More generally, various reagents and deposited products may be referred to sometimes hereinafter by alphabetic acronyms based on their constituent elements or moieties, e.g., PZT for lead zirconium titanate, BST for barium strontium titanate, etc., and in such case, such acronymic designations are intended to be broadly construed to encompass all suitable stoichiometric forms of the composition under consideration.

It is to be appreciated that the compositions disclosed herein, in respect of constituent components and/or moieties of such compositions, may comprise, consist, and/or consist essentially of, such constituent components and/or moieties.

Other aspects and features of the invention will be more fully apparent from the ensuing disclosure and appended claims.

DETAILED DESCRIPTION OF THE INVENTION, AND PREFERRED EMBODIMENTS THEREOF

The disclosures of the following prior applications and appertaining patents hereby are incorporated herein in their entirety: U.S. application Ser. No. 08/181,800 filed Jan. 18, 1994; U.S. application Ser. No. 07/981,141 filed Jul. 22, 1992, and issued Jan. 18, 1994 as U.S. Pat. No. 5,280,012; U.S. application Ser. No. 08/414,504 filed Mar. 31, 1995; U.S. application Ser. No. 08/280,143 filed Jul. 25, 1994; U.S. patent application Ser. No. 07/927,134, filed Aug. 7, 1992; U.S. patent application Ser. No. 07/807,807, filed Dec. 13, 1991, now issued as U.S. Pat. No. 5,204,314; U.S. patent application Ser. No. 07/549,389, filed Jul. 6, 1990; U.S. application Ser. No. 07/981,141 filed Jul. 22, 1992; U.S. application Ser. No. 07/615,303 filed Nov. 19, 1990; U.S. application Ser. No. 07/581,631 filed Sep. 12, 1990 in the names of Peter S. Kirlin, et al., and issued Jul. 6, 1993 as U.S. Pat. No. 5,225,561.

The present invention generally relates to metalorganic source reagent compositions, and liquid compositions containing such metal-organic source reagent compositions. More specifically, the metal source reagent compositions of the present invention comprise compounds or coordination complexes in which the metal atoms are coordinated to ligand species which are organic in character, as discussed in the preceding Summary section herein.

The ligand groups of the metal source complexes in the broad practice of the present invention may be variously substituted to realize a wide variety of materials to optimize volatility, stability and film purity. Preferably, when the metal source reagent comprises two or more metal source complexes in combination with one another, the ligands of the various metal source complexes should be either (a) identical to result in degenerative ligand exchange (wherein any ligand exchange involves replacement of the ligand group by the same type ligand from another constituent of the composition), or (b) resistant to any detrimental non-degenerative ligand exchange in relation to one another which would substantially impair or preclude the efficacy of the metal source complex for its intended purpose.

The ligand groups that are potentially useful in metal source reagents of the present invention include the ligands which are more fully disclosed in U.S. Pat. No. 5,225,561, the disclosure of which hereby is incorporated herein in its entirety.

The metal source reagents when utilized in solvent media are selected on the basis of the following criteria: (i) the metal centers in the coordinated complexes should be as coordinatively saturated as possible, and in such respect multidentate ligands are preferred which occupy multiple coordination sites in the source reagent complex; (ii) the ligands preferably comprise sterically bulky groups such as isopropyl, t-butyl, and neopentyl, which prevent close approach of the metal centers and thus hinder deleterious ligand exchange reactions which might otherwise occur; and (iii) each individual metal source reagent in the solution has a suitable vapor pressure characteristic, e.g., a vapor pressure of at least 0.001 Torr at the temperature and pressure conditions involved in their volatilization.

The solvent medium employed in source reagent solutions in accordance with the present invention may be any suitable organic solvent which is compatible with the metal complexes in the solution, has moderate volatility, and in which high concentrations of the metal complexes can be dissolved. Such solvent medium may suitably comprise one or more solvent species such as: glymes, aliphatic hydrocarbons, aromatic hydrocarbons, organic ethers (including dialkyl, cyclic and crown ethers), dialkyl esters, alkyl nitrites (=$NR_b$, wherein $R_b$ is H, $C_1$–$C_8$ alkyl, or $C_1$–$C_8$ perfluoroalkyl, e.g., trifluoroethyl), and alkanols. Among these classes of solvents, preferred solvent species include glyme solvents having from 1 to 20 ethoxy —($C_2H_4O$)— repeat units; $C_2$–$C_{12}$ alkanols, organic ethers selected from the group consisting of dialkyl ethers comprising $C_1$–$C_6$ alkyl moieties, $C_4$–$C_8$ cyclic ethers, and $C_{12}$–$C_{60}$ crown $O_4$–$O_{20}$ ethers wherein the prefixed $C_i$ range is the number i of carbon atoms in the ether compound and the suffixed $O_i$ range is the number i of oxygen atoms in the ether compound; $C_6$–$C_{12}$ aliphatic hydrocarbons; and $C_6$–$C_{18}$ aromatic hydrocarbons. Particularly preferred crown ethers include 12-crown-4, 15-crown-5, and 18-crown-6 species.

Preferred metal source reagent species include compounds having as constituent moieties thereof β-diketonate and alkoxide ligands, and a metal selected from the group consisting of Mg, Ca, Sr, Ba, Sc, Y, La, Ce, Ti, Zr, Hf, Pr, V, Nb, Ta, Nd, Cr, W, Pm, Mn, Re, Sm, Fe, Ru, Eu, Co, Rh, Ir, Gd, Ni, Th, Cu, Dy, Ho, Al, Tl, Er, Sn, Pb, Tm, Bi, Lu, Th, Pd, Pt, Ga, In, Au, Ag, Li, Na, K, Rb, Cs, Mo, and Yb, wherein the metal is coordinated to at least one alkoxide ligand and at least one β-diketonate ligand.

Illustrative β-diketonate ligands employed in metal source complexes of the present invention include acac, thd, fod, hfod, tfacac, and hfacac, and their corresponding thio analogs.

By way of example, the metal source reagent liquid solutions of the present invention may suitably comprise metal source reagent and solvent medium species identified in Table V set out below.

TABLE V

| Metal Source Reagent(s) | Solvent Medium |
|---|---|
| $Al(thd)_3$ | tetrahydrofuran with 10% tetraglyme; |
| $Al(OR)_3$ | tetrahydrofuran with 10% tetraglyme; |
| $Ba(thd)_2(tetraglyme)$, $Ca(thd)_2$, $Cu(thd)_2$ | 25:1 butyl acetate/tetraglyme; |
| $Ba(thd)_2(tetraglyme)$, $Sr(thd)_2(tetraglyme)$, $Ti(OiPr)_2(thd)_2$ | 25:1 butyl acetate/tetraglyme; |
| $Sr(thd)_2$ | 10:1 isopropanol/tetraglyme; |
| $Ca(thd)_2$ | |
| $Cr(thd)_3$ | 9:1 tetrahydrofuran/tetraglyme; |
| $Er(thd)_3$ | butyl acetate |
| $Ir(acac)_3$ or $Ir(thd)_3$ | butyl acetate |
| $La(thd)_3$ | tetrahydrofuran |
| $(MeO)_3P = O$ | |
| $MgAl_2(OiPr)_8$ | isopropanol |
| $Nb(OiPr)_4(thd)$ | 8:2:1 tetrahydrofuran/isopropanol/tetraglyme |
| $Pb(thd)_2$ | 9:1 tetrahydrofuran/tetraglyme; |
| $La(thd)_3$ | |
| $Ti(OiPr)_2(thd)_2$ | |
| $Pb(thd)_2$ | 9:1 tetrahydrofuran/tetraglyme; |
| $Ti(OiPr)_2(thd)_2$ | |
| $Pb(thd)_2$ | 8:2:1 tetrahydrofuran/isopropanol/tetraglyme |
| $Zr(thd)_4$ | |
| $Pb(thd)_2$ | 8:2:1 tetrahydrofuran/isopropanol/tetraglyme |
| $Zr(thd)_4$ | |
| $Ti(OiPr)_2(thd)_2$ | |
| $Ru(acac)_3$ or $Ru(thd)_3$ | butyl acetate |
| Sn (alkyl)$_2$ (β-diketonate)$_2$ alkyl = $C_1$—$C_8$ alkyl | butyl acetate |
| Sn (acetates)$_2$ | butyl acetate or 25:1 butyl acetate/tetraglyme |
| $Sr(thd)_2$ (tetraglyme) | 8:2:1 tetrahydrofuran/isopropanol/tetraglyme |
| $BiPh_3$ | |
| $Ta(OiPr)_4thd$ | |
| $Ta(OEt)_5$ | neat with 1% ethanol or ethanol |
| $[O = Ti(thd)_2]_n$ wherein n is 1 or 2 | butyl acetate or 25:1 butyl acetate/tetraglyme |
| $Y(thd)_3$ | isopropanol |
| $Y(thd)_3$ | 25:1 butyl acetate/tetraglyme |
| $Ba(thd)_2$ | |
| $Cu(thd)_2$ | |
| $Zr(thd)_4$ | 9:1 tetrahydrofuran/tetraglyme; |
| $Y(thd)_3$ | |
| $[O = Zr(thd)_2]_n$ wherein n is 1 or 2 | butyl acetate or 25:1 butyl acetate/tetraglyme |
| $Y(thd)_3$ | isopropanol |
| $Y(thd)_3$ | 25:1 butyl acetate/tetraglyme |
| $Ba(thd)_2$ | |
| $Cu(thd)_2$ | |
| $Zr(thd)_4$ | 9:1 tetrahydrofuran/tetraglyme; |
| $Y(thd)_3$ | |
| $[O = Zr(thd)_2]_n$ wherein n is 1 or 2 | butyl acetate or 25:1 butyl acetate/tetraglyme |
| $Cu(shfac)_2$ | 25:1 butyl acetate/tetraglyme |
| $Sr(shfac)_2$ | 25:1 butyl acetate/tetraglyme |
| $Sr(sthd)_2$ | 25:1 butyl acetate/tetraglyme |
| $Sr(sthd)_2$ | butyl acetate/tetrathiocyclodecane |
| $Ca(sthd)_2$ | 25:1 butyl acetate/tetraglyme |
| $Sr(sthd)_2$ | |
| $Ga(sthd)_3$ | |
| $Ce(sthd)_4$ | |
| $Ca(sthd)_2$ | 25:1 butyl acetate/tetraglyme |
| $Ga(sthd)_3$ | |
| $Ce(sthd)_4$ | |
| $Cu(shfac)_2$ | 8:25:1 isopropanol/tetrahydrofuran/tetraglyme |
| $Ca(sthd)_2$ | 25:1 butyl acetate/tetrathiocyclodecane |
| $Sr(sthd)_2$ | |
| $Ga(sthd)_3$ | |
| $Ce(sthd)_4$ | |

TABLE V-continued

| Metal Source Reagent(s) | Solvent Medium |
|---|---|
| Cu(hfac)$_2$ | 25:1 butyl acetate/tetraglyme |
| Sr(thd)$_2$ | 25:1 butyl acetate/tetrathiocyclodecane |
| Cu(hfac)$_2$ | 8:25:1 isopropanol/tetrahydrofuran/tetraglyme |
| Ti(hfac)$_3$ | 25:1 butyl acetate/tetraglyme |
| Ti(hfac)$_3$ | butyl acetate |
| Mo(hfac)$_3$ | butyl acetate |
| Mo(thd)$_3$ | butyl acetate |

The metal source reagent solutions employed in the process of the present invention may be readily employed in CVD applications for forming a metal-containing film on a substrate, by the steps of volatilizing the metal source reagent liquid solution to yield a metal source vapor, and contacting the metal source vapor with the substrate, to deposit the metal-containing film thereon. Illustrative metal source reagent solutions and corresponding metal-containing film compositions are identified in Tables III and hereinabove in the "Summary of the Invention" section hereof.

One class of source reagent compositions usefully employed in the process of the present invention includes source reagent liquid solutions comprising:

(i) at least one, and preferably at least two, metal coordination complexes, each of the formula:

wherein:

M is a metal selected from the group consisting of Mg, Ca, Sr, Ba, Sc, Y, La, Ce, Ti, Zr, Hf, Pr, V, Nb, Ta, Nd, Cr, W, Pm, Mn, Re, Sm, Fe, Ru, Eu, Co, Rh, Ir, Gd, Ni, Tb, Cu, Dy, Ho, Al, Tl, Er, Sn, Pb, Tm, Bi, Lu, Th, Pd, Pt, Ga, In, Au, Ag, Li, Na, K, Rb, Cs, Mo, and Yb;

A is selected from the group consisting of β-diketonates and β-ketoesters, and their sulfur and nitrogen analogs;

R is selected from the group consisting of $C_1$–$C_8$ alkyl, $C_2$–$C_8$ cycloalkyl, $C_2$–$C_{10}$ alkenyl, $C_2$–$C_{15}$ cycloalkenyl, $C_6$–$C_{10}$ aryl, and (fully or partially) fluorinated derivatives thereof (i.e., wherein hydrogen substituent(s) of the $C_1$–$C_8$ alkyl, $C_2$–$C_8$ cycloalkyl, $C_2$–$C_{10}$ alkenyl, $C_2$–$C_{15}$ cycloalkenyl, or $C_6$–$C_{10}$ aryl ligand, is/are replaced by fluorine substituent(s));

B is selected from the group consisting of polyethers, polyamines, polythiols, bipyridines, glymes, alcohols, crown ethers, crown thioethers, cyclic polyamines (cyclenes), thioglymes, arylthiols, and aliphatic thiols (mercaptans).

Q is hydrocarbyl or halohydrocarbyl, e.g., a ligand selected from the group consisting of $C_1$–$C_8$ alkyl, $C_2$–$C_8$ cycloalkyl, $C_2$–$C_{10}$ alkenyl, $C_2$–$C_{15}$ cycloalkenyl, $C_6$–$C_{10}$ aryl, and fluorinated derivatives thereof;

a, x, y, and z are stoichiometric coefficients for the ligands A, OR, B, and Q, respectively, wherein a is >1; each of x, y, and z is independently ≧0, and $A_a(OR)_xB_yQ_z$ is in stoichiometric relationship to metal M; and (ii) a solvent for the metal coordination complex(es).

Another class of source reagent solutions usefully employed in the process of the present invention contain β-diketonate alkoxide compounds having a metal M selected from the group consisting of Mg, Ca, Sr, Ba, Sc, Y, La, Ce, Ti, Zr, Hf, Pr, V, Nb, Ta, Nd, Cr, W, Pm, Mn, Re, Sm, Fe, Ru, Eu, Co, Rh, Ir, Gd, Ni, Tb, Cu, Dy, Ho, Al, Ti, Er, Sn, Pb, Tm, Bi, Lu, Th, Pd, Pt, Ga, In, Au, Ag, Li, Na, K, Rb, Cs, Mo, and Yb, complexed to at least one alkoxide ligand and at least one β-diketonate ligand, in which the compounds have the following formula:

$$M(OR^1)_x(R^2\!\!=\!\!C(G)\!\!-\!\!CH\!\!-\!\!C(G)\!\!-\!\!R^3)_y$$

wherein:

G is oxygen, sulfur, or imide of the formula: =$NR_b$, wherein $R_b$ is H, $C_1$–$C_8$ alkyl, Or $C_1$–$C_8$ perfluoroalkyl (e.g., trifluoroethyl);

x+y=p where p is the valence of metal M;

x+2y=q where q is the coordination number of the metal M;

$R^1$ is $C_1$–$C_6$ hydrocarbyl or fluoroalkyl;

$R^2$ and $R^3$ are independently selected from $C_1$–$C_{14}$ hydrocarbyl, $C_1$–$C_6$ alkoxy, and $C_2$–$C_6$ fluoroalkyl groups, wherein hydrocarbyl groups may be selected from $C_1$–$C_8$ alkyl, $C_6$–$C_{10}$ cycloalkyl, $C_2$–$C_{12}$ alkenyl and $C_6$–$C_{14}$ aryl groups, and $C_1$–$C_6$ fluoroalkyl groups may be selected from perfluoroalkyls of 2 through 6 carbons.

$R^1$ is preferably $C_1$–$C_6$ alkyl, preferably methyl, ethyl, propyl, n-propyl, i-propyl, n-butyl, s-butyl, or t-butyl, and most preferably ethyl, i-propyl, or t-butyl. $R^2$ and $R^3$ are preferably selected from the $C_2$–$C_6$ alkyl or cycloalkyl groups t-butyl, s-butyl, i-propyl, cyclohexyl, or neopentyl, and most preferably t-butyl, s-butyl, or isopropyl.

The various source reagent metal complexes employed in the practice of the invention may be readily made by conventional synthetic techniques, including those more fully described in U.S. Pat. No. 5,225,561, the disclosure of which hereby is incorporated herein by reference. The resulting reagent metal complexes may readily be formulated into solution form, by conventional dissolution and solubilization techniques, for subsequent use as CVD source reagents having good shelf life characteristics and which are substantially stable in storage at ambient conditions (e.g., room temperature). The reagent solutions may subsequently be readily vaporized by suitable reagent delivery systems such as those described in U.S. Pat. No. 5,204,314, the disclosure of which also is hereby incorporated herein by reference.

The features and advantages of the invention are more fully shown by the following non-limiting examples, wherein all parts and percentages are by weight unless otherwise expressly stated.

EXAMPLES I–XXXII of Prior Copending U.S. application No. 08/181,800

The Examples I–XXXII of prior copending U.S. application No. 08/181,800 are hereby incorporated herein by reference, and are supplemented in respect of the compositions hereinafter claimed, by the following Examples 1–47 hereof.

Example 1. Synthesis of Ta(OEt)$_4$($\eta^2$-thd)

One equivalent (33.9 g) of 2,2,6,6-tetramethyl-3,5-heptanedione (Hthd) was added directly to 74.6 g Ta(OEt)$_5$ in a 500 mL Schlenk flask; both starting materials were obtained commercially (Lancaster Chemicals, Inc.). The vessel was heated to 65° C. under a slow nitrogen purge to a bubbler. After 2 hours, the ethanol generated was removed in vacuo to yield 99.8 g of the colorless liquid Ta(OEt)$_4$($\eta^2$-thd) in quantitative yield, which solidified upon cooling. The compound melted at 26° C. and boiled at approximately 80° C. at 140 mtorr. The $^1$H and $^{13}$C NMR spectra in benzene-d$_6$ were consistent with an octahedral structure composed of two ethoxide ligands in axial positions and a second set of cis-ethoxide ligands in the equatorial plane across from the bidentate β-diketonate: d 5.81 (s, 1 H, CH), 4.72 (q, 4 H, CH$_2$), 4.20 (q, 4 H, CH$_2$), 1.34 (tr, 6 H, CH$_3$), 1.14 (tr, 6 H, CH$_3$), 1.13 (s, 18 H, t-Bu); $^{13}$C{$^1$H} NMR (C$_6$D$_6$) d 199.9 (CO), 92.9 (CH$_{diket}$), 68.8 (CH$_2$CH$_3$), 65.4 (CH$_2$CH$_3$), 40.9 (CMe$_3$), 28.3 (CMe), 19.6 (CHCH$_3$), 19.0 (CHH$_3$).

Example 2. Synthesis of Ta(OiPr)$_4$(η$^2$-thd)

A nine-fold excess of isopropanol (170 mL) was added to 33.6 g Ta(OEt)$_4$(η$^2$-thd). The solution was heated at 60° C. for 45 min, following which the volatiles were removed in vacuo. The ligand exchange procedure was repeated a second time to yield 36.8 g of white, crystalline Ta((O-i-Pr)$_4$(η$^2$- thd) in quantitative yield. The product was purified by sublimation at 100° C. at 150 mtorr. The compound melted at 149° C. The $^1$H and $^{13}$C NMR spectra in benzene-d$_6$ were consistent with an octahedral structure composed of two isopropoxide ligands in axial positions and a second set of cis-isopropoxide ligands in the equatorial plane across from the bidentate b-diketonate: d 5.81 (s, 1 H, CH), 5.10 (sept, 2 H, CH), 4.51 (sept, 2 H, CH), 1.38 (d, 12 H, Me), 1.20 (d, 12 H, Me), 1.17 (s, 18 H, t-Bu); $^{13}$C{$^1$H} NMR (C$_6$D$_6$) d 199.4 (CO), 93.0 (CH$_{diket}$), 75.0 (CHMe$_2$), 71.4 (CHMe$_2$), 40.8 (CMe$_3$), 28.3 (CMe$_3$), 26.4 (CHMe$_2$), 25.8 (CHMe$_2$).

Example 3. Synthesis of Nb(OEt)$_4$(η$^2$-thd)

The procedure of Example 1 is followed, using Nb(OEt)$_5$ as starting material rather than the tantalum ethoxide. One equivalent of 2,2,6,6-tetramethyl-3,5-heptanedione (Hthd) is added directly to Nb(OEt)$_5$ in a Schlenk flask. The vessel is heated to about 65° C. under a slow nitrogen purge to a bubbler. After 2 hours the ethanol generated is removed in vacuo to yield Nb(OEt)$_4$(η$^2$-thd) in quantitative yield.

Example 4. Synthesis of Nb(OiPr)$_4$(η$^2$-thd)

A nine-fold molar excess of isopropanol is added to Nb(OEt)$_4$(η$^2$-thd). The resulting solution is heated at 60° C. for 45 min, following which the volatiles are removed in vacuo. The ligand exchange procedure is repeated a second time to yield solid Nb(O-i-Pr)$_4$(η$^2$-thd) in quantitative yield. The product is purified by sublimation at 100° C. at 150 mtorr.

Example 5. Deposition of Niobia Film

Nb(O-i-Pr)$_4$(η$^2$-thd) is used to deposit Nb$_2$O$_5$ ("niobia") on a silicon wafer held at 400° C. in a CVD reactor. The Nb reagent is contained in a vessel ("bubbler") held at 185° C. and Ar gas is flowed through the vessel at 100 sccm. Pressure in the "bubbler" is controlled at 80 torr using a manual throttle valve. Oxygen is flowed to the reactor through a separate manifold at 300 sccm. Total pressure in the reactor is 1 torr and partial pressure of the Nb reagent in the reactor is 0.03 torr. Deposition rate is approximately 0.04 mm/minute.

Example 6. Deposition of Tantala Film

Ta(O-i-Pr)$_4$(thd) is used to deposit Ta$_2$O$_5$ (tantala) on a fused silica (glass) envelope of a high intensity lamp by chemical vapor deposition. The glass surface is held at 450° C. in a CVD reactor. The Ta(O-i-Pr)$_4$(thd) compound is dissolved in an organic solvent and this liquid solution is pumped to a vaporization zone of the reactor held at 200° C. where Ar carrier gas is also introduced at 100 sccm. At the vaporizer zone the solvent evaporates, the Ta compound sublimes and the gaseous reagents and Ar then flow to the chemical vapor deposition reactor. Oxygen is flowed to the reactor through a separate manifold at 300 sccm. Total pressure in the reactor is 1 torr and the deposition rate is 0.065 mm/minute.

Example 7. Deposition of Nb:BST

Nb(O-i-Pr)$_4$(η$^2$-thd) is used to deposit Ba$_{1-x}$Sr$_x$Ti$_{1-y}$Nb$_y$O$_3$ (Nb:BST) on a platinum metal layer on a silicon wafer in a CVD reactor. The metal layer will act as a bottom electrode in a capacitor and the Nb:BST film will have a high dielectric constant with dc low leakage current density. The platinum surface is held at 650° C. Nb(O-i-Pr)$_4$(η$^2$-thd) reagent is dissolved in an organic solvent along with Ba(thd)$_2$-tetraglyme, Sr(thd)$_2$-tetraglyme and Ti(OPr)$_2$(thd)$_2$, and this liquid solution is pumped to a vaporization zone held at 220° C. where Ar carrier gas is also introduced at 600 sccm. The solution is stable and no detrimental levels of ligand exchange occured between the metallorganic compounds in the liquid phase or gas phase. At the vaporization zone the solvent evaporates and the Bi, Sr, and Ti compounds sublime and pass into the vapor phase. The gaseous reagents and Ar then flow to the CVD reactor. A mixture of oxygen and nitrous oxide is flowed to the reactor through a separate manifold at 300 sccm each. Total pressure in the reactor is 0.700 torr and the (Nb:BST) is efficiently deposited.

Example 8. Deposition of Bi$_2$SrTa$_2$O$_9$

Ta(O-i-Pr)$_4$(thd) is used to deposit Bi$_2$SrTa$_2$O$_9$ on platinum metal layer on a silicon wafer in a CVD reactor. The Bi$_2$SrTa$_2$O$_9$ film will form a ferroelectric capacitor with remanent polarization that can be switched greater than 10$^{12}$ times. The Bi$_2$SrTa$_2$O$_9$ is deposited at 650° C. Ta(O-i-Pr)$_4$(thd) is dissolved in an organic solvent along with triphenylbismuth and Sr(thd)$_2$-tetraglyme and this liquid solution is pumped to a vaporization zone held at 200° C. where Ar carrier gas is also introduced at 100 sccm. The solution is stable and no detrimental ligand exchange occured between the metallorganic compounds in the liquid or gas phase. At the vaporization zone the solvent evaporates and the Bi, Sr, Na compounds sublime. The gaseous reagents and Ar then flow to the chemical vapor deposition reactor. A mixture of oxygen and nitrous oxide is flowed to the reactor through a separate manifold at 300 sccm each. Total pressure in the reactor is 2.1 torr and the Bi$_2$SrTa$_2$O$_9$ is deposited at useful rates.

Example 9. Growth of GMR Oxide Films on LaAlO$_3$ (100), NdGaO$_3$ (110), and MgO (100) Substrates by CVD La$_x$Ca$_{1-x}$MnO$_3$ films were grown on LaAlO$_3$ (100), NdGaO$_3$ (110), and MgO (100) substrates by CVD in the CVD system that is shown schematically in FIG. 1. Tris (tetramethylheptanedionato)lanthanum (La(thd)$_3$), bis(tetramethylheptanedionato)calcium (Ca(thd)$_2$), and tris (tetramethylheptane-dionato)manganese (Mn(thd)$_3$), all of which were purchased commercially (Strem Chemicals), were used as precursor materials. These three organic compounds, in appropriate amounts, were mixed and dissolved in a single organic solution of 25:1 butyl acetate:tetraglyme under an inert atmosphere. The concentrations of La(thd)$_3$, Ca(thd)$_2$ and Mn(thd)$_3$ in the solution were 0.033, 0.017, and 0.05 moles/liter of solution, respectively. During deposition, the solution was constantly injected into a vaporizer by a liquid pump and the vapors were carried immediately into a chemical vapor deposition reactor by nitrogen gas. The films were deposited at a constant pressure of 1.5 Torr and at a substrate temperature ranging from 600° C. to 700° C. Both oxygen and nitrous oxide were used as oxidants.

The films were characterized and showed a high transition temperature $T_c$ in the as-deposited films, probably due to the higher oxygen partial pressure in the CVD process. The highest $T_c$ attained was 300 K. The peak value of resistivity r is observed to decrease from 34 mΩ-cm to 12 mΩ-cm in the film with $T_c$=300 K. Post annealing of these films in 1 atm of $O_2$ further reduced r and increased $T_c$. The oxygen content plays an important role in controlling the carrier concentration. All of the films prepared at different substrate temperatures between 600 and 750° C. were highly (001) oriented. The grain size of films decreased as the substrate temperature decreased without a degradation of crystallinity determined by XRD in this temperature range. There was no correlation found between grain size and cusp temperature or magnetoresistance of the films. The preferred orientation of the films appear to affect on the temperature dependence of resistivity as shown in the case of a (LaCa)MnO3 film deposited on MgO substrate. A lower $\Delta R/R_H$ effect of as-deposited (LaCa)MnO3 films by MOCVD than that of annealed (LaCa)MnO3 films prepared by laser deposition is probably due to a relatively low resistivity of these MOCVD films.

Example 10. Growth of Zirconium Titanate

A number of PZT runs were performed with the objectives of optimizing vaporizer conditions and achieving desired film stoichiometry, from Zr(thd)$_4$ and Ti(O-iPr)$_4$ source reagents. The CVD reactor was constructed to permit preheating of the carrier gas using heat tape around an in-line filter, and the delivery system for vaporization and transport of the source reagent vapor was arranged and constructed in accordance with the disclosure of U.S. Pat. No. 5,204,314.

Initial experiments employed as the solvent a mixture of THF:tetraglyme in the ratio of 9:1. It was found that the effect of carrier gas preheat was minimal. Vaporizer temperature was a much stronger variable with increased vaporization temperature giving somewhat more consistent vaporization as judged by monitoring the pressure of the vaporizer behind the frit (vaporization element). Lower temperatures ($T_{vap}$=215° C.) resulted in more erratic vaporizer pressure. In addition, increased relative Zr content in the solution caused wide swings in vaporizer pressure as the run progressed, even at $T_{vap}$=230° C. (Total Zr content in all cases has been held at 0.15 to 0.145 moles/liter solution to prevent delivery tube clogging which was experienced at higher Zr concentrations.)

One variable studied in the test was the addition of isopropanol to the solvent. In such modification, the solvent used was THF:isopropanol:tetraglyme in the ratio of 8:2:1. IPA affected the process remarkably favorably in respect of the desired film composition. Zr incorporation efficiency increased to the point where films of $Zr_xTi_{1-x}O_4$ were produced. The deposition conditions were held constant during all of the experiments, evidencing the fact that transport of Zr is significantly enhanced by the addition of IPA to the THF/tetraglyme solvent. This suggested that ligand exchange may have played a role, e.g., with the reaction Zr(thd)$_4$→Zr(OiPr)$_x$(thd)$_{4-x}$, leading to more volatile species. It was also observed that the swings in vaporizer pressure decreased (at $T_{vap}$=230° C. and with 40 mm frits) with the modified solvent. Ligand exchange may also have led to the provision of all liquid precursors at the vaporizer temperature rather than solid as is the case for Zr(thd)$_4$.

Example 11. Growth of BiSrTa

Transport experiments for Bi-Sr-Ta were conducted in a CVD reactor to roughly determine vaporizer operating conditions, following which two Ta compounds were evaluated. The first was Ta(OiPr)$_4$(thd), for which three vaporizer temperatures were investigated. The best condition was found to be 200° C. A second Ta compound, Ta$_2$(OEt)$_4$(thd) also was tried under the same transport conditions, as summarized in Table V below.

TABLE V

| Frit pore size | 20 μm |
|---|---|
| Carrier gas flow | 450 sccm Ar (preheated) |
| Precursors | BiPh$_3$, Sr(thd)$_2$, and Ta(OiPr)$_4$(thd) or Ta(OEt)$_4$(thd) |
| Solvent | 8:2:1 THF:isopropanol:tetraglyme |
| Reagent solution concentrations | Bi 0.40M - Sr 0.15M - Ta 0.40M |
| Delivery rate | 0.1 ml/min |
| System base pressure | 2 torr |

Ta(OiPr)$_4$($\eta^2$-thd)

The 180° C. experiment resulted in a steep rise in pressure behind the frit, presumably due to unsublimed material (likely Sr(thd)$_2$) which was consistent with the fact that the pressure behind the frit recovered by 93% to nearly its initial value in about 1.5 hours.

The 200° C. experiment had a steep initial pressure rise, followed by the lowest steady-state rise of any of the conditions tried. A relatively low pressure recovery after the experiment (29%) indicated that some decomposition of metalorganic material occurred at the frit.

The 220° C. experiment behaved similarly to the 200° C. experiment with two exceptions: the steady state rise was >2× higher and a steep pressure rise occurred at the end of the experiment (~2 hours) which was accompanied by a clog in the delivery tube at the frit. The clog disappeared as the vaporizer cooled overnight and a significant amount (about a 5 mm dia. lump) of white material was present on top of the frit. This may have been due to the reagent being sucked into the vaporizer from the delivery tube (with some leakage through the 20 psi check valve) from which the solvent had evaporated. An NMR analysis was conducted on the material, and it showed BiPh$_3$ and Ta(OiPr)$_4$(thd) precursors in about their original ratios but no Sr(thd)$_2$.

The frit residue was analyzed qualitatively by x-ray fluorescence (XRF). The results showed that the amount of Bi and Ta left on the frit increased with increasing vaporizer temperature, as expected.

Ta(OEt)$_4$($\eta^2$-thd)

This compound appeared fairly well behaved until near the end of the transport experiment, where a significant rise in pressure behind the frit occurred, accompanied by a clog in the delivery system. This clog disappeared within minutes of shutting off the solution flow. Vaporizer pressure recovered by about 62% after the experiment.

Several films were deposited on Pt/Ta/SiO$_2$/Si during the transport experiments. Deposition at 750° C. susceptor temperature resulted in a film that was poorly crystallized. In contrast, films deposited at 800° C. showed strong XRD peaks. Interestingly, all films had a striped appearance across the wafer indicating changing thickness. This may be attributable to a macroscopic manifestation of ledge motion during growth of the compound which is known to be a layered structure. Fringes were observed moving across the wafer at the early stages of growth.

Example 12. Growth of BaTiO$_3$ from Ti(OR)$_2$(thd)$_2$

A source reagent mixture of Ti(OR)$_2$(acac)$_2$ and Ba(thd)$_2$ in solvent medium was found to experience ligand exchange, resulting in mixed Ba(β-diketonate)$_2$ species that display a reduced volatility. Use of Ti(OR)$_2$(thd)$_2$ in place of Ti(OR)$_2$(acac)$_2$ resulted in degenerate ligand exchange that was transparent to the vaporization and CVD deposition process.

Example 13. Growth of Bi$_2$SrTa$_2$O$_9$ Using Ta(OEt)$_4$(thd)

The combination of reagents Ta(OEt)$_5$ and Sr(thd)$_2$ also resulted in ligand exchange when the ligands were dissolved in solvent medium, as in Example 12. By using Ta(OEt)$_4$(thd) the aforementioned exchange problem is alleviated in solution. This enables a reproducible transport and CVD process.

The Ta(OEt)$_4$(thd) and Sr(thd)$_2$ solution can be used for depositing SrTaO or Bi$_2$SrTa$_2$O$_9$ materials.

Example 14. Growth of BaTiO$_3$ or BST Using Ti(OR)$_2$(thd)$_2$

The source reagent combination of Ti(OR)$_4$ and Ba(thd)$_2$ can undergo ligand exchange as described in Examples 12 and 13. Use of Ti(OR)$_2$(thd)$_2$ as the Ti reagent alleviates the exchange problem in solution. The latter solution can be used for the formation of BaTiO or BaSrTiO films.

Example 15. Growth of PbTiO$_3$

The source reagent combination of Ti(OR)4 and Pb(thd)$_2$ can also result in ligand exchange in solution. Using Ti(OR)$_2$(thd)$_2$ eliminates the ligand exchange with the Pb reagent. The latter solution is useful for deposition of PbTiO$_3$ or PbZrTiO$_3$ (PZT) films.

Example 16. Growth of YBCO

Y(thd)3, Ba(thd)2, and Cu(thd)$_2$ were dissolved in an appropriate solvent to enable the facile vaporization and gas-phase transport of the precursors into the reaction zone. The volatility and transport characteristics of the reagents are primarily governed by the thd ligands and the temperature of the heated vaporization zone of the liquid delivery system. These solutions can be used for YxBayCuzO film growth.

Example 17. Growth of YBCO

Various metal (β-diketonates) are dissolved in the desired solvent to provide compatible solubilities. For example, Cu(thd)$_2$ or Cu(hfacac)$_2$ reagents are used in tandem with the similar Y(thd)$_3$ or Y(hfacac)$_3$ reagents, respectively, to realize comparable solubilities of widely differing metals.

Example 18. CVD of Aluminum—Addition of Solvent to Decrease Precursor Viscosity An inert solvent is added to a "neat" liquid or reagent being used for film growth. Dimethyl aluminum hydride (dimer) is a viscous liquid that yields high-purity aluminum films. Liquid delivery is facilitated by dilution in an inert organic solvent, such as hexane or toluene. The dilute solution is easily transported to the vaporization zone for deposition. Other organic solvents with a suitable boiling point can be used with equal success.

Example 19. Solvent System to Optimize Liquid Delivery of Reactants for CVD

A solvent is chosen, such that preferential boiling of the solvent does not occur without volatilization of the reagent. This allows maximum volatilization of the reagent to be realized without detrimental clogging of the vaporizer. For example, the use of a tetrahydrofuran-isopropanol mixture is advantageous for the delivery vaporization of Bi(Ph)$_3$ and Ta(OiPr)$_4$(thd).

Example 20. Use of Additive to Increase Reactant Solubility for LP CVD

Acetone, tetrahydrofuran, dimethoxyethane (DME) or dimethylformamide (DMF) are added to a solution containing Ba(thd)$_2$ to maximize its solubility.

Example 21. Use of Polyethers to Improve Suitability for LP CVD

Various compositions were made up of reagent solutions, including: addition of 4-glyme to Ba(thd)$_2$; addition of polyamines for Ba(thd)$_2$; addition of polyether alcohols to enhance thermal stability of reagents; and addition of 18-crown-6 to enhance the thermal stability of the reagents.

Example 22. Use of Solvent to Lower Freezing Point of Low-Melting Solid

Ta(OEt)$_5$ has a melting point of ~21° C. Liquid delivery of this material requires a lowering of the freezing point to maintain a liquid in the bubbler and throughout the process system. Lowering the freezing point is achieved by addition of ethanol to the 'neat' Ta(OEt)$_5$ used to grow Ta$_2$O$_5$ films. The ethanol does not have a deterimental effect on the reagent, the liquid delivery or the reagent and/or the CVD growth process.

Example 23. Addition of Solvent to Depress Freezing Point of Low Melting Solids Ti(OiPr)4, m.p. of 20° C., is mixed with i-PrOH to lower the melting point. MgAl$_2$(OiPr)$_8$, m.p. 40° C., is mixed with iPrOH to lower the melting point. Ta(OEt)$_4$(thd), m.p.=26° C., is mixed with EtOH to lower the melting point.

Example 24. Liquid Delivery of Cu Reagents— Solvent Coordination for Altering Complex Properties A solvent is chosen to maximize dissolution of a reagent based upon the solubility of that precursor in a given solvent. However, the solvent may be chosen to provide a solvated complex which exhibits different physical properties after salvation. Cu(hfacac)$_2$ hydrate is exceedingly soluble in alcoholic solvents because the water is displaced and the alcohol coordinates to the metal center. Isolation of the solvated complex yields materials with different physical properties. Thus, the solvent is chosen to alter the physical and chemical properties of the reagent being used for film growth.

| Complex | Tm (° C.) | Tdec.(° C.) |
|---|---|---|
| Cu(hfacac)$_2$ (MeOH) | 134–138 | 250 |
| Cu(hfacac)$_2$ (EtOH) | 103–104 | 250 |
| Cu(hfacac)$_2$ (iPrOH) | 53–55 | 210 |

This same concept can be extended to a wide variety of other reagents which can be solvated to provide complexes of different physico-chemical properties for use in CVD. For example, tetrahydrofuran (THF) may be added to a solution to increase the solubility of Cu(thd)$_2$ therein.

Example 25. Use of Additive to Increase Reactant Stability for LP CVD

Tetraglyme was added to Ba(thd)$_2$(tetraglyme) solution to enhance thermal stability of the reagent composition.

Example 26. Addition of Excess Lewis Base to Increase Reactant Stability During LP CVD Lewis base copper(I) β-diketonate complexes are useful for copper CVD. However, the Lewis base may be easily liberated from the molecule resulting in pre-mature decomposition and clogging of the vaporizer. To combat this problem, excess Lewis base is added. Similarly, excess Lewis base can be added to stop the formation of a less volatile dinuclear species and eliminate precipitation in the vaporizer. For example, liberation of 3-hexyne from 3-hexyne Cu(hfacac) leads to the formation of a dinuclear complex, 3-hexyne [Cu(hfacac)]$_2$, which is a solid at room temperature. The formation and precipitation of this dinuclear solid can be controlled by forcing this equilibrium in the reverse direction. Thus, excess 3-hexyne not only enhances the thermal stability, but eliminates formation of a less volatile solid precipitate, which can lead to clogging and decomposition in the vaporizer.

Example 27. Addition of Polyether or Polyamine to Reduce Hydrolysis of Reactant During LP CVD The coordination of H$_2$O to Ba(thd)$_2$ on thermal vaporization may be reduced or eliminated by coordinating a stronger Lewis Base to the barium center.

Example 28. Formation of CuS-Based Films

A solution consisting of copper (II) bis (1,1,1,5,5,5-hexafluoro-2-thio-pentane-4-one) was dissolved in an organic solvent containing n-butyl acetate and tetraglyme (25:1). The solution was delivered to a warm-walled reactor using a liquid delivery system and reacted with H$_2$S to produce a copper sulfide (CuS) based film. This approach can be used to produce complex copper sulfides by co-reaction with a third reactant to produce films such as CuInS, CuGaS and CuSeS films.

Example 29. Formation of SrS Films in Presence of H$_2$S

A solution consisting of strontium (II) bis (2,2,6,6,-tetramethyl-3-thio-heptane-5-one) was dissolved in a solution of n-butyl acetate and tetraglyme (25:1). This solution was delivered, using a commercial liquid delivery system, to a CVD reactor and reacted with H$_2$S to produce high quality SrS films. These films can be used as a white phosphor layer for electroluminescent display applications.

Example 30. Formation of SrS Films With Thiol-Containing Source Solution

In a modification to Example 29, a solution consisting of strontium (II) bis (2,2,6,6,-tetramethyl-3-thio-heptane-5-one) was dissolved in a solution of n-butyl acetate and tetraglyme (25:1). This solution also contained a sulfur source, such as t-butylthiol or cyclohexyl thiol and was delivered (using a commercial liquid delivery system) to a CVD reactor to produce high quality SrS films. The incorporation of the thiol obviates the need for co-reaction with H$_2$S and therefore, is more desirable for health, safety and environmental reasons; this will facilitate manufacturing of SrS as a white phosphor layer for electroluminescent display applications.

Example 31. Formation of SrS Films in Presence of H$_2$S with Butyl Acetate/Tetrathiocyclodecane Solvent System In a modification to Examples 29 and 30, a solution consisting of strontium (II) bis (2,2,6,6,-tetramethyl-3-thioheptane-5-one) was dissolved in a solution of n-butyl acetate and tetrathiocyclodecane. This solution was delivered (using a commercial liquid delivery system) to a CVD reactor and co-reacted with H$_2$S to produce high quality SrS films. These films can be used as a white phosphor layer for electroluminescent display applications.

Example 32. Formation of Ce-Doped (Ca, Sr)Ga$_2$S$_4$ Films in Presence of H$_2$S In a separate approach, multi-component phosphors, such as Ce doped (Ca,Sr)Ga$_2$S$_4$ can be deposited by liquid delivery of one or more solutions containing the following co-reactants; Ca (II) bis (2,2,6,6,-tetramethyl-3-thio-heptane-5-one), Sr (II) bis (2,2,6,6,-tetramethyl-3-thio-heptane-5-one), Ga (III) tris (2,2,6,6,-tetramethyl-3-thioheptane-5-one) and Ce (IV) tetrakis (2,2,6,6,-tetramethyl-3-thioheptane-5-one). These reactants are dissolved into n-butyl acetate and tetraglyme (25:1) and delivered to the CVD reactor for Ce doped (Ca,Sr)Ga$_2$S$_4$ film growth with H$_2$S as the sulfur source. The concentrations of each component can be controlled via the concentration of the individual components in solution or via mixing of individual solutions of the reactants. The resulting thiogallate film can be used for electroluminescent films in display applications.

Example 33. Formation of Ce-Doped (Ca, Sr)Ga$_2$S$_4$ Films With Thiol-Containing Solvent System In a modification of Example 32, a Ce doped (Ca,Sr) Ga$_2$S$_4$ film can be deposited by liquid delivery of one or more solutions containing the following co-reactants; Ca (II) bis (2,2,6,6,-tetramethyl-3-thio-heptane-5-one), Sr (II) bis (2,2,6,6,-tetramethyl-3-thio-heptane-5-one), Ga (III) tris (2,2,6,6,-tetramethyl-3-thio-heptane-5-one) and Ce (IV) tetrakis (2,2,6,6,-tetramethyl-3-thio-heptane-5-one). These reactants are dissolved into n-butyl acetate, tetraglyme (25:1) and sulfur containing source, such as t-butyl thiol or cyclohexyl thiol. The incorporation of the thiol obviates the need for coreaction with H$_2$S and therefore, is more desirable for manufacturing and environmental reasons.

Example 34. Formation of Ce-Doped (Ca, Sr)Ga$_2$S$_4$ Films With Thiol-Containing Solvent System and Deposition in the Presence of Hydrogen Sulfide Gas In a modification of Examples 32 and 33, a Ce doped (Ca,Sr)Ga$_2$S$_4$ film can be deposited by liquid delivery of one or more solutions containing the following co-reactants; Ca (II) bis (2,2,6,6,-tetramethyl-3-thioheptane-5-one), Sr (II) bis (2,2,6,6,-tetramethyl-3-thioheptane-5-one), Ga (III) tris (2,2,6,6,-tetramethyl-3-thioheptane-5-one) and Ce (IV) tetrakis (2,2,6,6,-tetramethyl-3-thioheptane-5-one). These reactants are dissolved into n-butyl acetate, tetrathiollcyclodecane and delivered to the CVD reactor for Ce doped (Ca,Sr)Ga$_2$S$_4$ film growth with H$_2$S as the sulfur source. The concentrations of each component can be controlled via the concentration of the individual components in solution or via mixing of individual solutions of the reactants. The resulting thiogallate film can be used for electro-luminescent films in display applications.

Example 35. Formation of CuS Films, and Binary Metal Sulfide Films

A solution consisting of copper (II) bis (1,1,1,5,5,5-hexafluoro-2,4-pentanedionato) was dissolved in an organic solvent containing i-propanol, tetrahydrofuranacetate and tetraglyme (2:8:1). The solution was delivered to a warm-walled reactor using a liquid delivery system and reacted with $H_2S$ to produce a copper sulfide based film. In a modification of this method, the sulfur source is t-butylthiol, octanethiol or cyclohexylthiol and is a component of the solution. This approach can be used to produce complex copper sulfides by co-reaction with a third reactant to produce films such as CuInS, CuGaS and CuSeS films for a variety of applications.

Example 36. Formation of CuS Films, and Binary Metal Sulfide Films

A solution consisting of copper (II) bis (1,1,1,5,5,5-hexafluoro-2-,4-pentanedione) was dissolved in an organic solvent containing n-butyl acetate and tetraglyme (25:1). The solution was delivered to a warm-walled reactor using a liquid delivery system and reacted with $H_2S$ to produce a copper sulfide (CuS) based film. This approach can be used to produce complex copper sulfides by co-reaction with a third reactant to produce films such as CuInS, CuGaS and CuSeS films.

Example 37. Formation of SrS Films

A solution consisting of strontium (II) bis (2,2,6,6,-tetramethyl-3,5-heptanedione) was dissolved in a solution of n-butyl acetate and tetraglyme (25:1). This solution was delivered, using a commercial liquid delivery system, to a CVD reactor and reacted with $H_2S$ to produce high quality SrS films. These films can be used as a white phosphor layer for electroluminescent display applications.

Example 38. Formation of SrS Films

In a modification to Example 29, a solution consisting of strontium (II) bis (2,2,6,6,-tetramethyl-3,5-heptanedione) was dissolved in a solution of n-butyl acetate and tetraglyme (25:1). This solution also contained a sulfur source, such as t-butylthiol or cyclohexyl thiol and was delivered (using a commercial liquid delivery system) to a CVD reactor to produce high quality SrS films. The incorporation of the thiol obviates the need for co-reaction with $H_2S$ and therefore, is more desirable for health, safety and environmental reasons; this will facilitate manufacturing of SrS as a white phosphor layer for electroluminescent display applications.

Example 39. Formation of SrS Films

In a modification to Examples 29 and 30, a solution consisting of strontium (II) bis (2,2,6,6,-tetramethyl-3,5-heptanedione) was dissolved in a solution of n-butyl acetate and tetrathiocyclodecane. This solution was delivered (using a commercial liquid delivery system) to a CVD reactor and co-reacted with $H_2S$ to produce high quality SrS films. These films can be used as a white phosphor layer for electroluminescent display applications.

Example 40. Formation of Ce-Doped (Ca, Sr)$Ga_2S_4$ Films in the Presence of Hydrogen Sulfide Gas In a separate approach, multi-component phosphors, such as Ce doped (Ca,Sr)$Ga_2S_4$ can be deposited by liquid delivery of one or more solutions containing the following co-reactants; Ca (II) bis (2,2,6,6,-tetramethyl-3,5-heptanedione), Sr (II) bis (2,2,6,6,-tetramethyl-3,5-heptanedione), Ga (III) tris (2,2,6,6,-tetramethyl-3,5-heptanedione) and Ce (IV) tetrakis (2,2,6,6,-tetramethyl-3,5-heptanedione). These reactants are dissolved into n-butyl acetate and tetraglyme (25:1) and delivered to the CVD reactor for Ce doped (Ca,Sr)$Ga_2S_4$ film growth with $H_2S$ as the sulfur source. The concentrations of each component can be controlled via the concentration of the individual components in solution or via mixing of individual solutions of the reactants. The resulting thiogallate film can be used for electro-luminescent films in display applications.

Example 41. Formation of Ce-Doped (Ca, Sr)$GaS_4$ Films With Thiol-Containing Solvent System In a modification of Example 32, a Ce doped (Ca,Sr)$Ga_2S_4$ film can be deposited by liquid delivery of one or more solutions containing the following co-reactants; Ca (II) bis (2,2,6,6,-tetramethyl-3,5-heptanedione), Sr (II) bis (2,2,6,6,-tetramethyl-3,5-heptanedione), Ga (III) tris (2,2,6,6,-tetramethyl-3,5-heptanedione) and Ce (IV) tetrakis (2,2,6,6,-tetramethyl-3,5-heptane-dione). These reactants are dissolved into n-butyl acetate, tetraglyme (25:1) and sulfur containing source, such as t-butyl thiol, octylthiol or cyclohexyl thiol. The incorporation of the thiol obviates the need for co-reaction with $H_2S$ and therefore, is more desirable for manufacturing and environmental reasons.

Example 42. Formation of Ce-Doped (Ca, Sr)$GaS_4$ Films With Thiol-Containing Solvent System and Deposition in the Presence of Hydrogen Sulfide Gas In a modification of Examples 32 and 33, a Ce doped (Ca,Sr)$Ga_2S_4$ film can be deposited by liquid delivery of one or more solutions containing the following co-reactants; Ca (II) bis (2,2,6,6,-tetramethyl-3,5-heptanedione), Sr (II) bis (2,2,6,6,-tetramethyl-3,5-heptanedione), Ga (III) tris (2,2,6,6,-tetramethyl-3,5-heptanedione) and Ce (IV) tetrakis (2,2,6,6,-tetramethyl-3,5-heptane-dione). These reactants are dissolved into n-butyl acetate, tetrathiacyclodecane and delivered to the CVD reactor for Ce doped (Ca,Sr)$Ga_2S_4$ film growth with $H_2S$ as the sulfur source. The concentrations of each component can be controlled via the concentration of the individual components in solution or via mixing of individual solutions of the reactants. The resulting thiogallate film can be used for electroluminescent films in display applications.

Example 43. Formation of CuS Films With Thiol-Containing Solvent System and Deposition in the Presence of Hydrogen Sulfide Gas, and Production of Films of Binary Metal Sulfide Films A solution consisting of copper (II) bis (1,1,1,5,5,5-hexafluoro-2,4-pentanedionato) in an organic solvent containing i-propanol, tetrahydrofuranacetate and tetraglyme (2:8:1). The solution was delivered to a warm-walled reactor using a liquid delivery system and reacted with $H_2S$ to produce a copper sulfide based film. In a modification of this method, the sulfur source is t-butylthiol, octanethiol or cyclohexylthiol and is a component of the solution. This approach can be used to produce complex copper sulfides by co-reaction with a third reactant to produce films such as CuInS, CuGaS and CuSeS films for a variety of applications.

Example 44. Formation of $TiS_2$ Films With Thiol-Containing Solvent System or Deposition in the Presence of Hydrogen Sulfide Gas A solution consisting of titanium (III) tris (1,1,1,5,5,5-hexafluoro-2,4-pentanedionato) dissolved in an organic solvent was delivered to a warm walled CVD reactor using a liquid delivery system. The precursor was reacted with H$_2$S to deposit yellow films of TiS$_2$ as a lubricating layer onto metal parts. The process may be varied by using organic thiols in the solution and thus, obviates the need for H$_2$S co-reactant. This latter process is desirable for health, safety and environmental reasons.

Example 45. Formation of TiS$_2$ Films With Thiol-Containing Solvent System or Deposition in the Presence of Hydrogen Sulfide Gas A solution consisting of titanium (III) tris (2,2,6,6-tetramethyl-3,5-heptanedionato) dissolved in n-butylacetate and was delivered to a warm walled CVD reactor using a liquid delivery system. The precursor was reacted with H$_2$S to deposit yellow films of TiS$_2$ as a lubricating layer onto metal parts. The process may be modified by using organic thiols, such as t-butyl thiol, octylthiol and cyclohexylthiol, in the solution and thus, obviates the need for co-reactanting with H$_2$S. This latter process is desirable for health, safety and environmental reasons and enables full scale manufacturing to be safely realized.

Example 46. Formation of MoS$_2$ Films With Thiol-Containing Solvent System or Deposition in the Presence of Hydrogen Sulfide Gas A solution consisting of molybdenum (III) tris (1,1,1,5,5,5-hexafluoro-2,4-pentanedionato) dissolved in n-butylacetate and was delivered to a warm walled CVD reactor using a liquid delivery system. The precursor was reacted with H$_2$S to deposit yellow films of MoS$_2$ as a lubricating layer onto metal parts. The process may be varied by using organic thiols in the solution and thus, obviates the need for H$_2$S co-reactant. This latter process is desirable for health, safety and environmental reasons.

Example 47. Formation of MoS$_2$ Films With Thiol-Containing Solvent System or Deposition in the Presence of Hydrogen Sulfide Gas A solution consisting of molybdenum (III) tris (2,2,6,6-tetramethyl-3,5-heptanedionato) dissolved in n-butyl acetate and was delivered to a warm walled CVD reactor using a liquid delivery system. The precursor was reacted with H$_2$S to deposit films of MoS$_2$ as a lubricating layer onto metal parts. The process may be varied by using organic thiols in the solution and thus, obviates the need for H$_2$S co-reactant . This latter process is desirable for health, safety and environmental reasons.

While the invention has been described herein with reference to specific embodiments, features and aspects, it will be recognized that the invention is not thus limited, but rather extends in utility to other modifications, variations, applications, and embodiments, and accordingly all such other modifications, variations, applications, and embodiments are to be regarded as being within the spirit and scope of the invention.

What is claimed is:

1. A method of forming a metal-containing film on a substrate, comprising the steps of:
   providing a metal source reagent composition comprising at least one metalorganic complex whose metal constituent is a metal component of the metal-containing film, and a solvent or suspending agent;
   volatilizing the metal source reagent composition to yield a metal source vapor;
   contacting the metal source vapor with a substrate under chemical vapor deposition conditions to deposit the metal-containing film on the substrate, wherein said metal source reagent composition comprises a metalorganic complex of the formula:

MA$_y$X 

wherein:
   M is a y-valent metal;
   A is a monodentate or multidentate organic ligand coordinated to M which allows complexing of MA$_y$ with X;
   y is an integer having a value of 2, 3 or 4;
   each of the A ligands may be the same or different; and
   X is a mono dentate or multidentate ligand coordinated to M and containing one or more atoms independently selected from the group consisting of atoms of the elements C, N, H, S, O and F.

2. The method of claim 1, wherein M is selected from the group consisting of Cu, Ba, Sr, La, Nd, Ce, Pr, Sm, Eu, Th, Gd, Tb, Dy, Ho, Er, Tm, Yb, Lu, Bi, Tl, Y, Pb, Ni, Pd, Pt, Al, Ga, In, Ag, Au, Co, Rh, Ir, Fe, Ru, Sn, Li, Na, K, Rb, Cs, Ca, Mg, Ti, Zr, Hf, V, Nb, Ta, Cr, Mo, W, Sc, La, Pr, Pm, Mn, Re, Tb, and Yb.

3. The method of claim 1, wherein A is selected from the group consisting of β-diketonates, β-thioketonates, β-diiminates, β-ketoesters, β-thioesters, β-ketoiminates, cyclopentadienyls, alkyls, perfluoroalkyls, alkoxides, perfluoroalkoxides, and Schiff bases.

4. The method of claim 1, wherein A is selected from the group consisting of β-diketonates, β-thioketonates, β-ketoesters, β-thioesters, and cyclopentadienyls.

5. The method of claim 1, wherein A is a β-diketonate.

6. The method of claim 1, wherein A is selected from the group consisting of:
   (i) 2,2,6,6-tetramethyl-3,5-heptanedionate;
   (ii) 1,1,1,5,5,5-hexafluoro-2,4-pentanedionate;
   (iii) 1,1,1,2,2,3,3-heptafluoro-7,7-dimethyl-4,6-octanedionate;
   (iv) cyclopentadienyl;
   (v) 4,4'-(ethane-1,2-diyldiimino) bis (3-pentene-2-one);
   (vi) pentamethylcyclopentadienyl;
   (vii) 2,4-pentanedionate; and
   (viii) 1,1,1 -trifluoro-2,4-pentanedionate.

7. The method of claim 1, wherein X is selected from the group consisting of:
   (i) oxyhydrocarbyl ligands;
   (ii) nitrogenous oxyhydrocarbyl ligands;
   (iii) fluorooxyhydrocarbyl ligands; and
   (iv) thiooxyhydrocarbyl ligands.

8. The method of claim 1, wherein X is selected from the group consisting of:
   (a) amines and polyamines;
   (b) bipyridines;
   (c) ligands of the formula:

wherein G is —O—, —S—, or —NR—, wherein R is H or hydrocarbyl;

(d) crown ethers;

(e) thioethers; and (f) ligands of the formula:

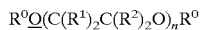

wherein:

$R^0$=H, methyl, ethyl, n-propyl, cyanato, perfluoroethyl, perfluoro-n-propyl, or vinyl;

$R^1$=H, F, or a sterically acceptable hydrocarbyl substituent;

$R^2$=H, F, or a sterically acceptable hydrocarbyl substituent;

n=2, 3, 4, 5, or 6; and each $R^0$, $R^1$, and $R^2$ may be the same as or different from the other $R^0$, $R^1$, and $R^2$, respectively.

9. The method of claim 1, wherein X is selected from the group consisting of tetraglyme, tetrahydrofuran, bipydridine, and 18-crown-6 ethers.

10. The method of claim 1, wherein X comprises a liquid of the formula:

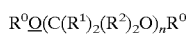

wherein:

$R^0$=H, methyl, ethyl, n-propyl, cyanato, perfluoroethyl, perfluoro-n-propyl, or vinyl;

$R^1$=H, F, or a sterically acceptable hydrocarbyl substituent;

$R^2$=H, F, or a sterically acceptable hydrocarbyl substituent;

n=2, 3, 4, 5, or 6; and each $R^0$, $R^1$, and $R^2$ may be the same as or different from the other $R^0$, $R^1$, and $R^2$, respectively.

11. The method of claim 1, wherein X comprises a ligand of the formula:

wherein:

each $R^0$, $R^1$, and $R^2$ is selected independently, and $R^0$=H, $CH_3$, or $C_2H_5$;

$R^1$ and $R^2$=H or F.

12. The method of claim 1, wherein: A is a β-diketonate; and X is tetraglyme, 18-crown-6 ether, bipyridine, or tetrahydrofuran.

13. The method of claim 1, wherein A is 2,2,6,6-tetramethyl-3,5-heptanedionate.

14. The method of claim 1, wherein the ligand X is tetrahydrofuran.

15. The method of claim 1, wherein A is selected from the group consisting of: β-diketonates, β-thioketonates, β-ketoiminates, β-diiminates, $C_1$–$C_8$ alkyl, $C_2$–$C_{10}$ alkenyl, $C_2$–$C_{15}$ cycloalkenyl, $C_6$–$C_{10}$ aryl, and $C_1$–$C_8$ alkoxy.

16. The method of claim 1, wherein the solvent includes at least one solvent species selected from the group consisting of: glymes, aliphatic hydrocarbons, aromatic hydrocarbons, ethers, esters, nitriles, and alcohols.

17. The method of claim 1, wherein the solvent comprises at least one solvent species selected from the group consisting of: glyme solvents having from 1 to 20 ethoxy —($C_2H_4$O)— repeat units; $C_2$–$C_{12}$ alkanols, organic ethers selected from the group consisting of dialkyl ethers comprising $C_1$–$C_6$ alkyl moieties, $C_4$–$C_8$ cyclic ethers, and $C_{12}$–$C_{60}$ crown $O_4$–$O_{20}$ ethers wherein the prefixed $C_i$ range is the number i of carbon atoms in the ether compound and the suffixed $O_i$ range is the number i of oxygen atoms in the ether compound; $C_6$–$C_{12}$ aliphatic hydrocarbons; and $C_6$–$C_{18}$ aromatic hydrocarbons.

18. The method of claim 1, wherein the metal source reagent composition includes $MA_y$ and solvent components selected from the group of $MA_y$ and associated solvent consisting of:

| $MA_y$ | associated solvent |
|---|---|
| Cu(shfac)$_2$ | 85–99% butyl acetate and 1–15% tetraglyme |
| Sr(shfac)$_2$ | 85–99% butyl acetate and 1–15% tetraglyme |
| Sr(sthd)$_2$ | 85–99% butyl acetate and 1–15% tetraglyme |
| Sr(sthd)$_2$ | 85–99% butyl acetate and 1–15% tetrathiocyclodecane |
| Ca(sthd)$_2$ | 85–99% butyl acetate and 1–15% tetraglyme |
| Sr(sthd)$_2$ | |
| Ga(sthd)$_3$ | |
| Ce(sthd)$_4$ | |
| Ca(sthd)$_2$ | 85–99% butyl acetate and 1–15% tetraglyme |
| Ga(sthd)$_3$ | |
| Ce(sthd)$_4$ | |
| Ca(sthd)$_2$ | 85–99% butyl acetate and 1–15% tetrathiocyclodecane |
| Sr(sthd)$_2$ | butyl acetate and cyclohexylthiol |
| Ga(sthd)$_3$ | butyl acetate and t-butylthiol |
| Ce(sthd)$_4$ | |
| Cu(shfac)$_2$ | 45–88% tetrahydrofuran |
| | 10–35% isopropanol |
| | 2–20% tetraglyme |
| Cu(hfac)$_2$ | 85–99% butyl acetate and 1–15% tetraglyme |
| Sr(thd)$_2$ | 85–99% butyl acetate and 1–15% tetraglyme |
| Sr(thd)$_2$ | 85–99% butyl acetate and 1–15% tetrathiocyclodecane |
| Sr(thd)$_2$ | tetrahydrofuran |
| Cu(hfac)$_2$ | 45–88% tetrahydrofuranacetate |
| | 10–35% isopropanol |
| | 2–20% tetraglyme |
| Ti(hfac)$_3$ | 85–99% butyl acetate and 1–15% tetraglyme |
| | butyl acetate and cyclohexylthiol |
| Ti(hfac)$_3$ | butyl acetate and t-butylthiol |
| Mo(hfac)$_3$ | butyl acetate and t-butylthiol |
| Mo(thd)$_3$ | butyl acetate and cyclohexylthiol |

19. The method of claim 1, wherein $MA_y$ comprises a metal β-diketonate compound and said solvent includes at least one solvent species selected from the group consisting of glymes, aliphatic hydrocarbons, aromatic hydrocarbons, ethers, esters, nitriles and alcohols.

20. The method of claim 19, wherein the metal moiety of said metal β-diketonate source compound is selected from the group consisting of Cu, Ba, Sr, Ca, Ga, Bi, Pb, Zr, Ce, Ti, Ta and Mo.

21. The method of claim 1, wherein the metal M is selected from the group consisting of Cu, Ba, Sr, La, Nd, Ce, Pr, Sm, Eu, Th, Gd, Tb, Dy, Ho, Er, Tm, Yb, Lu, Bi, Tl, Y, Pb, Ni, Pd, Pt, Al, Ga, In, Ag, Au, Co, Rh, Ir, Fe, Ru, Sn, Li, Na, K, Rb, Cs, Ca, Mg, Ti, Zr, Hf, V, Nb, Ta, Cr, Mo, W, Sc, La, Pr, Pm, Mn, Re, Tb, and Yb; A is selected from the group consisting of β-diketonates, β-thioketonates, β-diiminates, β-ketoesters, β-thioesters, β-ketoiminates, cyclopentadienyls, alkyls, perfluoroalkyls, alkoxides, perfluoroalkoxides, and Schiff bases; and X is selected from the group consisting of tetraglyme, tetrahydrofuran, bipyridine, crown ether, and thioether.

22. A method according to claim 1, wherein said metal-containing film on a substrate comprises a film of a complex metal oxide selected from the group consisting of barium titanate, barium strontium titanate, strontium bismuth tantalate, and lead zirconium titanate.

23. A method according to claim 1, wherein said metal-containing film on a substrate comprises a film of barium strontium titanate.

24. A method according to claim 1, wherein said metal-containing film on a substrate comprises a film of strontium bismuth tantalate.

25. A method according to claim 23, wherein the solvent comprises tetrahydrofuran.

26. A method according to claim 24, wherein the solvent comprises tetrahydrofuran.

27. A method of forming a barium strontium titanate film on a substrate, comprising conducting liquid delivery metalorganic chemical vapor deposition (MOCVD) using barium beta-diketonate and strontium beta-diketonate adducts in solvent as precursors, wherein said precursors are volatilized to form barium- and strontium-containing vapor therefrom, and contacting said vapor with the substrate under conditions yielding the barium strontium titanate film on the substrate.

28. A method of preparing a metal source reagent composition for use in liquid delivery chemical vapor deposition to form a metal-containing film on a substrate, said method comprising the steps of:
   providing a material including metal and organic constituents, wherein the metal constituent is a metal component of the metal-containing film, said material being selected from the group consisting of:
   (a) $MA_y$,
   (b) $MA_yX$ and
   (c) precursors and components of $MA_y$ and $MA_yX$;
   wherein:
      M is a y-valent metal;
      A is a monodentate or multidentate organic ligand coordinated or coordinatable to M which allows complexing of $MA_y$ with X;
      y is an integer having a value of 2, 3 or 4;
      each of the A ligands may be the same or different; and
      X is a monodentate or multidentate ligand coordinated or coordinatable to M and containing one or more atoms independently selected from the group consisting of atoms of the elements C, N, H, S, O and F, and
   introducing said material into a solvent or suspending agent that:
      (1) forms a metal source reagent composition containing the metalorganic complex $MA_yX$; and
      (2) is volatilizable to form a metal-containing vapor from such metal source reagent composition under liquid delivery chemical vapor deposition conditions.

29. The method of claim 28, wherein said material is introduced into a solvent, and said material and solvent react in situ in said solvent to form said metalorganic complex $MA_yX$.

30. The method of claim 28, wherein X is a coordinating solvent ligand.

31. The method of claim 28, wherein the metal M is selected from the group consisting of Cu, Ba, Sr, La, Nd, Ce, Pr, Sm, Eu, Th, Gd, Tb, Dy, Ho, Er, Tm, Yb, Lu, Bi, Ti, Y, Pb, Ni, Pd, Pt, Al, Ga, In, Ag, Au, Co, Rh, Ir, Fe, Ru, Sn, Li, Na, K, Rb, Cs, Ca, Mg, Ti, Zr, Hf, V, Nb, Ta, Cr, Mo, W, Sc, La, Pr, Pm, Mn, Re, Tb, and Yb.

32. The method of claim 28, wherein A is selected from the group consisting of β-diketonates, β-thioketonates, β-diiminates, β-ketoesters, β-thioesters, β-ketoiminates, cyclopentadienyls, alkyls, perfluoroalkyls, alkoxides, perfluoroalkoxides, and Schiff bases.

33. The method of claim 28, wherein A is selected from the group consisting of β-diketonates, β-thioketonates, β-ketoesters, β-thioesters, and cyclopentadienyls.

34. The method of claim 28, wherein A is a β-diketonate.

35. The method of claim 28, wherein A is selected from the group consisting of:
   (i) 2,2,6,6-tetramethyl-3,5-heptanedionate;
   (ii) 1,1,1,5,5,5-hexafluoro-2,4-pentanedionate;
   (iii) 1,1,1,2,2,3,3-heptafluoro-7,7-dimethyl-4,6-octanedionate;
   (iv) cyclopentadienyl;
   (v) 4,4'-(ethane-1,2-diyldiimino) bis (3-pentene-2-one);
   (vi) pentamethylcyclopentadienyl;
   (vii) 2,4-pentanedionate; and
   (viii) 1,1,1-trifluoro-2,4-pentanedionate.

36. The method of claim 28, wherein X is selected from the group consisting of:
   (i) oxyhydrocarbyl ligands;
   (ii) nitrogenous oxyhydrocarbyl ligands;
   (iii) fluorooxyhydrocarbyl ligands; and
   (iv) thiooxyhydrocarbyl ligands.

37. The method of claim 28, wherein X is selected from the group consisting of:
   (a) amines and polyamines;
   (b) bipyridines;
   (c) ligands of the formula:

wherein G is —O—, —S—, or —NR—, wherein R is H or hydrocarbyl;
   (d) crown ethers;
   (e) thioethers; and
   (f) ligands of the formula:

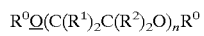

wherein:
      $R^0$=H, methyl, ethyl, n-propyl, cyanato, perfluoroethyl, perfluoro-n-propyl, or vinyl;
      $R^1$=H, F, or a sterically acceptable hydrocarbyl substituent;
      $R^2$=H, F, or a sterically acceptable hydrocarbyl substituent;
      n=2, 3, 4, 5, or 6; and
      each $R^0$, $R^1$, and $R^2$ may be the same as or different from the other $R^0$, $R^1$, and $R^2$, respectively.

38. The method of claim 28, wherein X is selected from the group consisting of tetraglyme, tetrahydrofuran, bipydridine, and 18-crown-6 ethers.

39. The method of claim 28, wherein X comprises a liquid of the formula:

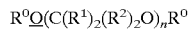

wherein:
      $R^0$=H, methyl, ethyl, n-propyl, cyanato, perfluoroethyl, perfluoro-n-propyl, or vinyl;
      $R^1$=H, F, or a sterically acceptable hydrocarbyl substituent;
      $R^2$=H, F, or a sterically acceptable hydrocarbyl substituent;
      n=2, 3, 4, 5, or 6; and
      each $R^0$, $R^1$, and $R^2$ may be the same as or different from the other $R^0$, $R^1$, and $R^2$, respectively.

40. The method of claim 28, wherein X comprises a ligand of the formula:

$$R^0O(C(R^1)_2C(R^2)_2O)_4R^0$$

wherein:

each $R^0$, $R^1$, and $R^2$ is selected independently, and
$R^0$=H, $CH_3$, or $C_2H_5$;
$R^1$ and $R^2$=H or F.

41. The method of claim 28, wherein: A is a β-diketonate; and X is tetraglyme, 18-crown-6 ether, bipyridine, or tetrahydrofuran.

42. The method of claim 28, wherein A is 2,2,6,6-tetramethyl-3,5-heptanedionate.

43. The method of claim 28, wherein the ligand X is tetrahydrofuran.

44. The method of claim 28, wherein A is selected from the group consisting of:

β-diketonates, β-thioketonates, β-ketoiminates, β-diiminates, $C_1$–$C_8$ alkyl, $C_2$–$C_{10}$ alkenyl, $C_2$–$C_{15}$ cycloalkenyl, $C_6$–$C_{10}$ aryl, <u>and</u> $C_1$–$C_8$ alkoxy.

45. The method of claim 28, wherein the solvent includes at least one solvent species selected from the group consisting of: glymes, aliphatic hydrocarbons, aromatic hydrocarbons, ethers, esters, nitrites, and alcohols.

46. The method of claim 28, wherein the solvent comprises at least one solvent species selected from the group consisting of: glyme solvents having from 1 to 20 ethoxy —($C_2H_4O$)— repeat units; $C_2$–$C_{12}$ alkanols, organic ethers selected from the group consisting of dialkyl ethers comprising $C_1$–$C_6$ alkyl moieties, $C_4$–$C_8$ cyclic ethers, and $C_{12}$–$C_{60}$ crown $O_4$–$O_{20}$ ethers wherein the prefixed Ci range is the number i of carbon atoms in the ether compound and the suffixed $O_i$ range is the number i of oxygen atoms in the ether compound; $C_6$–$C_{12}$ aliphatic hydrocarbons; and $C_6$–$C_{18}$ aromatic hydrocarbons.

47. The method of claim 28, wherein the metal source reagent composition includes $MA_y$ and solvent components selected from the group of $MA_y$ and associated solvent consisting of:

| $MA_y$ | associated solvent |
|---|---|
| Cu(shfac)$_2$ | 85–99% butyl acetate and 1–15% tetraglyme |
| Sr(shfac)$_2$ | 85–99% butyl acetate and 1–15% tetraglyme |
| Sr(sthd)$_2$ | 85–99% butyl acetate and 1–15% tetraglyme |
| Sr(sthd)$_2$ | 85–99% butyl acetate and 1–15% tetrathiocyclodecane |
| Ca(sthd)$_2$ | 85–99% butyl acetate and 1–15% tetraglyme |
| Sr(sthd)$_2$ | |
| Ga(sthd)$_3$ | |
| Ce(sthd)$_4$ | |
| Ca(sthd)$_2$ | 85–99% butyl acetate and 1–15% tetraglyme |
| Ga(sthd)$_3$ | |
| Ce(sthd)$_4$ | |
| Ca(sthd)$_2$ | 85–99% butyl acetate and 1–15% tetrathiocyclodecane |
| Sr(sthd)$_2$ | butyl acetate and cyclohexylthiol |
| Ga(sthd)$_3$ | butyl acetate and t–butylthiol |
| Ce(sthd)$_4$ | |
| Cu(shfac)$_2$ | 45–88% tetrahydrofuran 10–35% isopropanol 2–20% tetraglyme |
| Cu(hfac)$_2$ | 85–99% butyl acetate and 1–15% tetraglyme |
| Sr(thd)$_2$ | 85–99% butyl acetate and 1–15% tetraglyme |
| Sr(thd)$_2$ | tetrahydrofuran |
| Sr(thd)$_2$ | 85–99% butyl acetate and 1–15% tetrathiocyclodecane |
| Cu(hfac)$_2$ | 45–88% tetrahydrofuranacetate 10–35% isopropanol 2–20% tetraglyme |
| Ti(hfac)$_3$ | 85–99% butyl acetate and 1–15% tetraglyme butyl acetate and cyclohexylthiol |
| Ti(hfac)$_3$ | butyl acetate and t-butylthiol |
| Mo(hfac)$_3$ | butyl acetate and t-butylthiol |
| Mo(thd)$_3$ | butyl acetate and cyclohexylthiol. |

48. The method of claim 28, wherein $MA_y$ comprises a metal β-diketonate compound and said solvent includes at least one solvent species selected from the group consisting of glymes, aliphatic hydrocarbons, aromatic hydrocarbons, ethers, esters, nitriles and alcohols.

49. The method of claim 48, wherein the metal moiety of said metal β-diketonate source compound is selected from the group consisting of Cu, Ba, Sr, Ca, Ga, Bi, Pb, Zr, Ce, Ti, Ta and Mo.

50. The method of claim 28, wherein the metal M is selected from the group consisting of Cu, Ba, Sr, La, Nd, Ce, Pr, Sm, Eu, Th, Gd, Tb, Dy, Ho, Er, Tm, Yb, Lu, Bi, TI, Y, Pb, Ni, Pd, Pt, Al, Ga, In, Ag, Au, Co, Rh, Ir, Fe, Ru, Sn, Li, Na, K, Rb, Cs, Ca, Mg, Ti, Zr, Hf, V, Nb, Ta, Cr, Mo, W, Sc, La, Pr, Pm, Mn, Re, Th, and Yb; A is selected from the group consisting of β-diketonates, βthioketonates, β-diiminates, β-ketoesters, β-thioesters, β-ketoiminates, cyclopentadienyls, alkyls, perfluoroalkyls, alkoxides, perfluoroalkoxides, and Schiff bases; and X is selected from the group consisting of tetraglyme, tetrahydrofuran, bipyridine, crown ether, and thioether.

* * * * *

UNITED STATES PATENT AND TRADEMARK OFFICE
CERTIFICATE OF CORRECTION

PATENT NO. : 6,126,996
DATED : October 3, 2000
INVENTOR(S) : Peter S. Kirlin, et. al.

It is certified that error appears in the above-identified patent and that said Letters Patent is hereby corrected as shown below:

In the Abstract change "which allows complexing of MAY" to -- which allows complexing of $MA_Y$ --

In the Abstract change "Gd, Th, Dy, Ho" to -- Gd, Tb, Dy, Ho --

Column 3, line 40 change " Th " to -- Tb --

Column 4, line 38 change " MAY" to -- $MA_Y$ --

Column 5, line 62 change " Th, Gd, Th" to -- Th, Gd, Tb --

Column 6, line 28 change " Ni, Th, Cu" to -- Ni, Tb, Cu --

Column 11, line 63 change " Th" to -- Tb --

Column 12, line 49 change " nitrites" to -- nitriles --

Column 15, line 40 change " nitrites" to -- nitriles --

Column 15, line 58 change "Th" to -- Tb --

UNITED STATES PATENT AND TRADEMARK OFFICE
CERTIFICATE OF CORRECTION

PATENT NO. : 6,126,996
DATED : October 3, 2000
INVENTOR(S) : Peter S. Kirlin, et. al.

It is certified that error appears in the above-identified patent and that said Letters Patent is hereby corrected as shown below:

Column 17, line 57 change "$>1$" to -- $\geq 1$ --

Column 17, line 66 change "Ti" to -- Tl --

Column 18, line 5 change " $M(OR^1)_x(R^2=C(G)-CH-C(G)-R^3)_Y$" to -- $M(OR^1)_x(R^2=C(G)-CH-C(G)-R^3)_Y$ --

Column 19, line 7 change "19.0 $(CH_2H_{c3})$" to -- 19.0 $(CH_2CH_3)$

Column 23, line 42 change "YxBayCuzO" to -- $Y_xBa_yCu_zO$ --

Column 24, line 48 change "salvation" to -- solution --

Column 36, line 42 change "Th" to -- Tb --

Column 33, line 55 change " Ti" to -- Tl --

Signed and Sealed this

Twenty-second Day of May, 2001

Attest:

NICHOLAS P. GODICI

*Attesting Officer*  *Acting Director of the United States Patent and Trademark Office*